United States Patent [19]

Hasumi et al.

[11] Patent Number: 5,618,496
[45] Date of Patent: Apr. 8, 1997

[54] GAS SENSORS AND THEIR MANUFACTURING METHODS

[75] Inventors: Kazuhisa Hasumi, Odawara; Kentaro Nagano, Yokohama; Shuuichi Kamiyama, Tokyo; Hiroaki Yanagida, 1-3-19, Sasumachi, Choufu-shi, Tokyo; Osamu Okada, Osaka, all of Japan

[73] Assignees: Hiroaki Yanagida; Mikuni Corporation, both of Tokyo; Osaka Gas Co., Ltd., Osaka, all of Japan

[21] Appl. No.: 406,097

[22] Filed: Mar. 16, 1995

Related U.S. Application Data

[62] Division of Ser. No. 117,025, filed as PCT/JP93/00012, Jan. 8, 1993, abandoned.

[30] Foreign Application Priority Data

Jan. 10, 1992 [JP] Japan ............................. 4-3294

[51] Int. Cl.⁶ .................................................. G01N 27/12
[52] U.S. Cl. ........................... 422/90; 422/98; 340/634; 73/31.06
[58] Field of Search ........................... 422/90, 94, 98; 73/23.31, 335.04, 335.05, 31.06; 340/634

[56] References Cited

U.S. PATENT DOCUMENTS

| | | |
|---|---|---|
| 4,203,946 | 5/1980 | Ryerson ............................. 422/98 |
| 4,209,477 | 6/1980 | Yanagida et al. . |
| 4,259,292 | 3/1981 | Ichinose et al. ..................... 422/98 |
| 4,587,104 | 5/1986 | Yannopoulos . |
| 4,885,929 | 12/1989 | Kasahara et al. .................. 422/98 X |
| 5,055,270 | 10/1991 | Consadori et al. ................. 422/98 |

FOREIGN PATENT DOCUMENTS

| | | |
|---|---|---|
| 57-44847 | 3/1982 | Japan . |
| 58-30648 | 2/1983 | Japan . |
| 62-90528 | 4/1987 | Japan . |
| 62-90529 | 4/1987 | Japan . |

*Primary Examiner*—Jeffrey Snay
*Attorney, Agent, or Firm*—Cushman, Darby & Cushman LP Group of Pillsbury Madison & Sutro LLP

[57] ABSTRACT

P-type semiconductor 15 and n-type semiconductor 16 are formed as thick films or spray-coated onto electrodes 13 and 14 on top of substrates 11 and 12, with films of p-type semiconductor 15 and n-type semiconductor 16 being formed in such manner that they are in mutual contact. If a gas to be detected is introduced to the contact region while a bias voltage is being applied between the two electrodes, an output will be obtained in accordance with the concentration of flammable gas components in the gas being detected. In addition, if a film is formed from a material comprising a mixture of particles of p-type semiconductor and particles of n-type semiconductor, the bias voltage can be an AC voltage.

15 Claims, 36 Drawing Sheets characteristic of
SiC/ZnO p − n mixed sensor 115
p-n mixed
thick film injecting nozzle

GAS SENSORS AND THEIR MANUFACTURING METHODS

This is a division of application No. 08/117,025, filed Dec. 16, 1993, now abandoned, which is a 371 of application No. PCT/JP93/00012, filed Jan. 8, 1993.

TECHNICAL FIELD

This invention is utilized for the detection of gases present in trace amounts in a gas. In particular, it relates to gas sensors which will detect carbon monoxide, carbon dioxide, hydrogen, hydrocarbons and other target gases.

This invention is widely applicable to general domestic or business premises which utilize fuel gas, to workings where mining or other underground operations are carried out, to industrial sites where gases are manufactured or refined, and to facilities where petroleum products are transported or refined, etc.

This invention can be utilized for process control based on gas detection.

BACKGROUND TECHNOLOGY

Gas sensors which give a warning before gases leaking into the atmosphere reach a dangerous level and cause an explosion or become harmful to the human body have been widely known for a considerable time. In particular, carbon monoxide is dangerous to the human body or other living organisms even when it is present in air in trace amounts that are far smaller than the amounts required to cause an explosion, and it is therefore essential to have something that will generate an alarm when carbon monoxide is present at several hundred ppm.

Hitherto, technology employing ceramic semiconductor substances has been developed for gas sensors for this purpose. For example, a detailed account of this technology is given in:

Citation 1: Miyayama and Yanagida: "A Zinc Oxide Gas Sensor" *Seramikkusu* (*Ceramics Japan*), Vol. 18, No. 11 (November 1983), pp. 941–945, published by the Ceramic Society of Japan This technology utilizes the property that if a reducing gas comes into contact with the surface of a ceramic semiconductor, the height and width of the potential barrier will decrease as a result of the adsorbed oxygen that is present at the surface of the semiconductor reacting with the gas, which will lead to movement of electrons becoming easier and resistivity decreasing.

One of the inventors of the invention disclosed in this application also noticed that the rectifying junctions of a metal and a semiconductor, or of two different ceramic semiconductors, react with hydrogen gas or steam, and has suggested that a promising technique for the future would be to utilize changes in rectifying characteristics for the detection of hydrogen or water vapour in the air. An account of this appears in:

Citation 2: Miyayama and Yanagida: "New Developments in Gas Sensor Materials" *Denki Kagaku* (*Electrochemistry*), Vol. 50, No. 1 (January 1982), pp. 92–98 or;

Citation 3: Yanagida et al.: "Current-Voltage Characteristics of Semiconductor Junctions as Functions of Relative Humidity" *Japanese Journal of Applied Physics*, Vol. 22, No. 12, (December 1983), p. 1933

Although one of the inventors of the invention disclosed in this application suggested in the above-noted well-known publications that semiconductor junctions with rectifying characteristics would be effective for the detection of hydrogen gas and water vapour in the air, at that stage the working of such a device had not been fully elucidated, and so it was not clear what kinds of gases could be detected, nor what techniques or device configurations could be utilized for practical applications.

Some of the applicants of the present application have previously filed a patent application for a gas detection method and a gas sensor which can selectively detect target gases at low temperature, and this application has been laid open to public inspection as:

Citation 4: Japanese Patent Application Disclosure No. 62-90529.

This publication teaches (i) bringing into mechanical contact, by way of a contact surface, two types of solid substance which have rectifying properties when brought into mutual contact, (ii) forming gaps at this contact surface, and then (iii) introducing a sample gas into these gaps. Given this arrangement, the type of gas to which the device is sensitive varies with change in bias voltage. This is thought to be because the energy level of the potential barrier at the surface of these semiconductor substances changes to a different value.

The aforementioned group of applicants also filed a patent application for the detection of carbon dioxide using a construction equivalent to that set forth in Citation 4, and this application has been laid open to public inspection as:

Citation 5: Japanese Patent Application Disclosure No. 62-90528.

The object of the present invention is to provide gas sensors which represent a further improvement of the gas sensors disclosed in Citations 4 and 5 above, which have practical characteristics, and which are suited to mass production. More specifically, the object of the present invention is to provide gas sensors which exhibit stable characteristics and with which good sensor performance is obtained by having (i) improved circulation of the sample gas around the contact region and (ii) increased area of contact between the semiconductor contact region and the gas.

DISCLOSURE OF THE INVENTION

According to a first aspect, the present invention is a gas sensor characterized in that a p-type semiconductor film and an n-type semiconductor film in contact with one another have each been formed on a substrate as thick films. The term thick film as used here signifies a film formed by coating or by printing, with subsequent firing or drying; or alternatively, a film formed by spray coating.

Any of $CuO$, $NiO$, $CoO$, $Cr_2O_3$, $Cu_2O$, $MoO_2$, $Ag_2O$, $Bi_2O_3$, $Pr_2O_3$, $MnO$ or $SiC$, or combinations thereof, can be used as the p-type semiconductor. Any of $MgO$, $Al_2O_3$, $SiO_2$, $V_2O_5$, $Fe_2O_3$, $SrO$, $Nb_2O_5$, $Nb_2O_4$, $Nb_2O_3$, $BaO$, $Ta_2O_3$, $Ta_2O_5$, $CeO_2$, $ZnO$, $TiO_2$, $SnO_2$, $WO_3$, $Nd_2O_3$, $SiC$, $BaTiO_3$, $PbTiO_3$ or $SrTiO_3$, or combinations thereof, can be used as the n-type semiconductor. Although most of these materials are generally classified as insulators, this applies to their behaviour at room temperature, and within a certain range of higher temperatures they exhibit semiconductor properties.

The semiconductor films can contain one or more of the following materials as additives: $Li_2O$, $Al_2O_3$, $SiO_2$, $Nb_2O_5$, $Cr_2O_3$, $CaO$, $La_2O_3$ or $Ga_2O_3$.

It is desirable to provide a means for preventing gases reaching any part other than the contact region of the two semiconductors.

According to a second aspect, the present invention is a manufacturing method for this gas sensor, and is characterized in that a first pasty substance, the main constituent of which is particles of a p-type semiconductor material, and a second pasty substance, the main constituent of which is particles of an n-type semiconductor material, are coated or printed in such manner as to be respectively in contact with two electrodes which have been formed on the surface of an electrically insulating substrate, and in such manner that said first and second pasty substances are in mutual contact; and further characterized in that these pasty substances are then fired. This manufacturing method can be based on spray coating. That is to say, it is characterized in that a first pasty substance the main constituent of which is particles of a p-type semiconductor material, and a second pasty substance the main constituent of which is particles of an n-type semiconductor material, are spray-coated in such manner as to be respectively in contact with two electrodes which have been formed on the surface of an electrically insulating substrate, and in such manner that said first and second pasty substances are in mutual contact.

According to a third aspect, the present invention is a gas sensor characterized in that (i) particles of a p-type semiconductor material and particles of an n-type semiconductor material are kneaded so that they are in mutual contact and are then formed into a solid; (ii) two electrodes are provided on this solid, and (iii) there is a structure whereby gases containing the gas to be detected are introduced to the contact regions of the aforementioned particles.

According to a fourth aspect, the present invention is a manufacturing method for such a gas sensor, and is characterized in that a kneaded pasty substance containing particles based on a p-type semiconductor material and also particles based on an n-type semiconductor material is coated or printed in such manner as to be in contact with electrodes which have been formed on the surface of an electrically insulating substrate; and further characterized in that this pasty substance is fired. This manufacturing method can be based on spray coating. That is to say, a kneaded pasty substance containing particles based on a p-type semiconductor material and also particles based on an n-type semiconductor material is spray-coated in such manner as to be in contact with electrodes which have been formed on the surface of an electrically insulating substrate.

The preparation of the pasty substance will now be explained (see FIG. 47 and FIG. 48). The pasty substance comprises a solid particle component and a vehicle, with the vehicle being added in the range 5–200 parts by weight to 100 parts by weight of the solid particles, thereby enabling film thickness during coating or printing to be controlled. This also makes it possible to control the porosity that develops when the thick film is fired. The vehicle may be a solution obtained by dissolving ethyl cellulose or other cellulose derivative in an organic solvent. Ethyl cellulose improves the coating properties, and factors such as the viscosity of the pasty substance and its firing temperature are taken into consideration when selecting the composition and quantity of solvent. The solid particle component comprises particles of a p-type semiconductor material and/or particles of an n-type semiconductor material plus glass powder or other additive. The mix proportion of semiconductor particles to additive is selected in the range 5–95 wt %. Solid particles and vehicle weighed out in this proportion are subjected to preliminary kneading, after which secondary or tertiary agglomerations of particles are broken up. Fine kneading is then carried out to disperse the solid particles more uniformly throughout the vehicle, and a final kneading may also be employed to increase the uniformity.

An automatic mortar or mortar grinder, which is an automated mortar and pestle type kneading device, is used for the preliminary kneading. A triple roll mill was used to break up secondary or tertiary agglomerations of solid particles. Final kneading is carried out to increase the uniformity of the solid particles. An automatic mortar or mortar grinder is used for this final kneading as well.

To form the pasty substance into a thick film, the pasty substance may be printed onto the substrate, which can be done using the well-known method generally referred to as screen printing. Thick films can also be obtained by applying the pasty substance to the substrate with an applicator, etc.

Next, the film formed by coating or printing is subjected to preliminary drying. This volatilizes the solvent and prevents flow-out of the coating. Preliminary drying may be carried out at any temperature from 100° C. to 200° C. for 1–30 minutes. To volatilize the vehicle component so that only the solids remain, the main drying is carried out next for 1–60 minutes at a roughly constant temperature between 200° C. and 350° C. This is followed by firing at any temperature between 350° C. and 1450° C. for 5–180 minutes.

In the gas sensors set forth in Citation 4 and Citation 5 above, bulk material or thin films were used for the p-type semiconductors and n-type semiconductors. When the inventors associated with this application tried manufacturing a gas sensor using a thick film instead of bulk material or a thin film, they discovered that outstandingly good characteristics can be obtained, and thorough investigations of this culminated in the perfecting of the present invention. A thick film is a film formed by coating or printing followed by firing or drying. Alternatively, it may be a film formed by spray coating. In the case of semiconductors, thick films are obtained by printing and firing (or spray coating) a pasty substance obtained by kneading 0.1 μm–20 μm size particles. Compared with the prior art, wherein semiconductors fired and formed as bulk materials were brought into contact mechanically, a thick film formed in the foregoing manner has the following outstanding advantages:

(1) a stable p-n contact region is formed and stable characteristics are exhibited;

(2) because the thick film or the substrate is porous, the gas to be detected is introduced efficiently to the p-n contact region;

(3) because the area of contact between the p-n contact region and the gas is increased, good characteristics are exhibited.

P-type semiconductor thick films and n-type semiconductor thick films may be formed side by side on one and the same substrate, or they may be arranged so that they will come into contact with one another after being formed on separate substrates.

It was also found that by mixing together particles of a p-type semiconductor and particles of an n-type semiconductor, said particles can be brought into contact with one another within a film, in which case a gas sensor may be constructed by introducing the gas to be tested into the resulting contact regions. This is outstanding as a practical construction, since it is particularly stable.

When p-type semiconductor thick films and n-type semiconductor thick films have been formed separately, it is usual for a forward-biased voltage to be applied to their contact regions and for the target gas to be detected by changes in the resulting current. When particles of p-type semiconductor and particles of n-type semiconductor have been mixed together, there is no forward and backward distinction between the semiconductor particles, and so an AC bias voltage can be utilized.

The electrodes may be provided between the substrate and the semiconductor thick films, or they may be provided on the surface of the semiconductor thick films. It is convenient to employ thick film formation for the electrodes as well.

BEST CONFIGURATIONS FOR IMPLEMENTING THE INVENTION

First Embodiment

Figure 1:
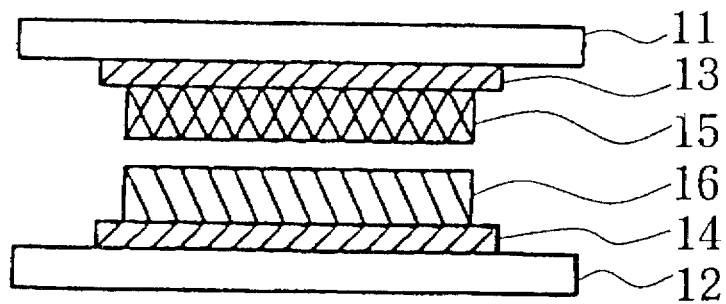
FIG. 1 shows a gas sensor according to a first embodiment of this invention.
Figure 2:
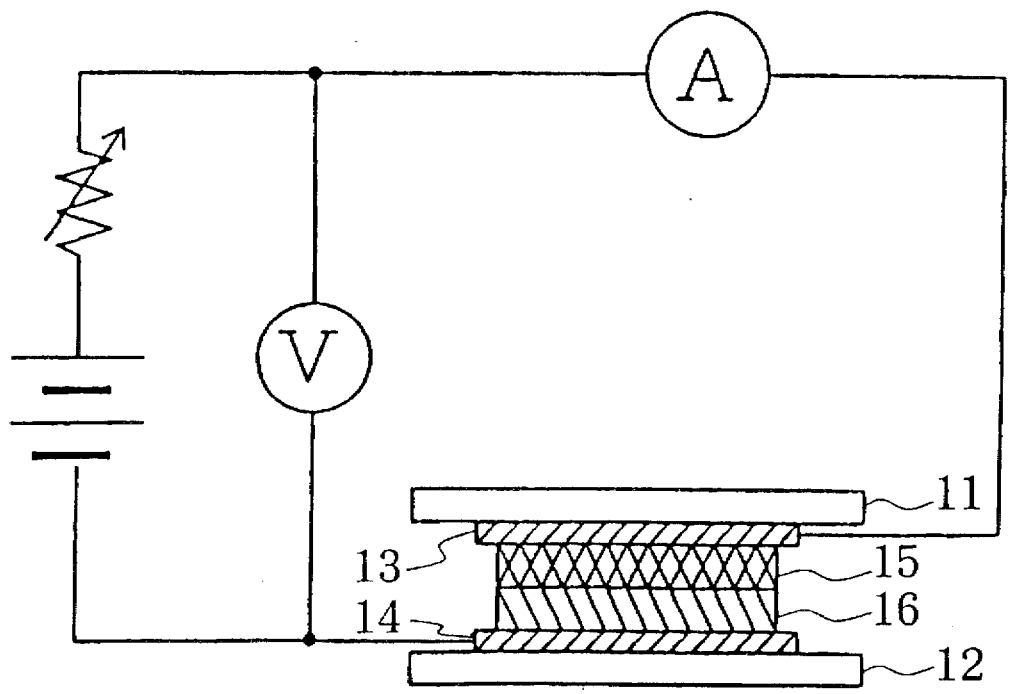
FIG. 2 shows this first embodiment in service.

FIG. 1 shows a gas sensor according to a first embodiment of this invention, and FIG. 2 shows this sensor in service. In both of these figures, the structure of the sensor is shown with the contact region between the p-type semiconductor thick film and the n-type semiconductor thick film seen from the side.

In this embodiment, electrode 13 is provided on the surface of substrate 11 and p-type semiconductor thick film 15 is provided in such manner as to be connected to this electrode 13. Separate substrate 12 is provided in addition to substrate 11, and electrode 14 is provided on the surface of this substrate, with n-type semiconductor thick film 16 provided on the surface of this electrode 14. P-type semiconductor thick film 15 and n-type semiconductor thick film 16 are brought into mechanical contact and form a structure wherein a gas containing the gas to be detected can be introduced into the resulting contact region.

The distinguishing feature of this embodiment is that p-type semiconductor thick film 15 and n-type semiconductor thick film 16 are both formed as thick films. That is to say, p-type semiconductor thick film 15 is a film which has been formed by printing a pasty substance, the main solid constituent of which is particles of a p-type semiconductor material, onto substrate 11 in such manner that it is in contact with electrode 13, and then firing this pasty substance. Likewise, n-type semiconductor thick film 16 is a film which has been formed by printing a pasty substance, the main solid constituent of which is particles of an n-type semiconductor material, onto substrate 12 in such manner that it is in contact with electrode 14, and then firing this pasty substance.

In this embodiment, firing may be carried out after the pasty substances that have been printed on substrate 11 and substrate 12, respectively, have been dried and then placed on top of one another so as to be in mutual contact. If this procedure is followed, the two semiconductor thick films 15 and 16 can be mechanically fixed together at the same time as they are brought into contact with one another.

As shown in FIG. 2, to make this embodiment operate, a positive DC voltage is applied to p-side electrode 13 and a negative DC voltage is applied to n-side electrode 14; in other words, a forward bias voltage is applied. Operation under these circumstances is equivalent in principle to that of the device set forth in aforementioned Citation 1, and utilizes the fact that the value of the current flowing in the contact region changes when a gas containing the gas to be detected is introduced into the contact region of the two semiconductor thick films 15 and 16.

Figure 3:
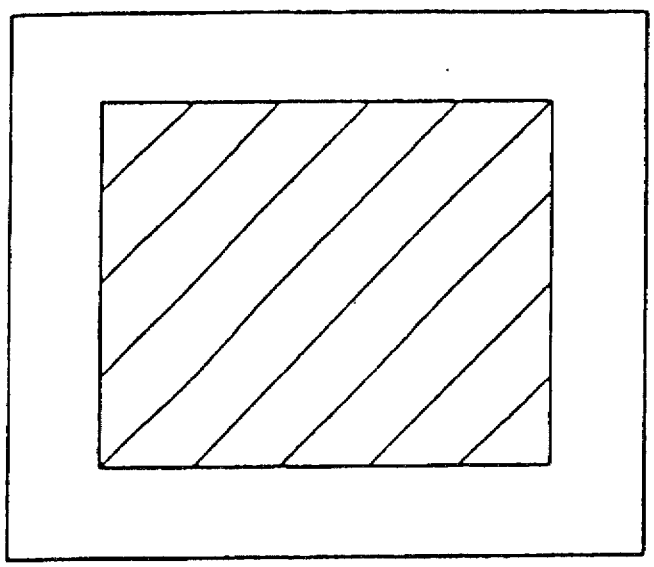
FIG. 3 shows an example of an electrode pattern.
Figure 4:
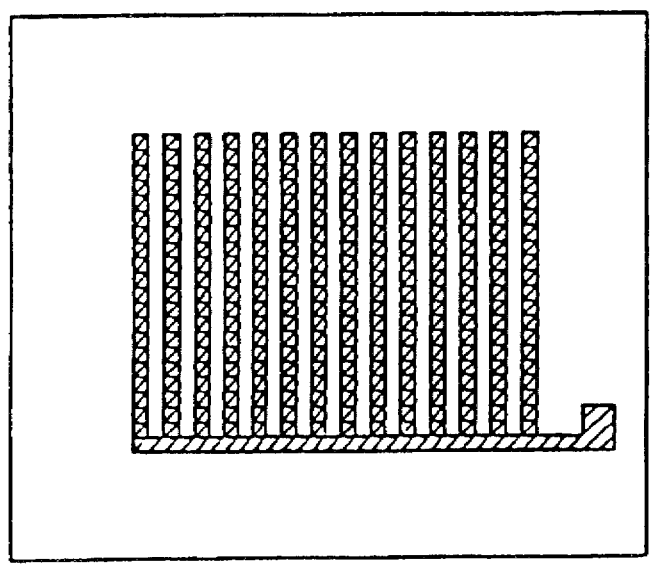
FIG. 4 shows another example of an electrode pattern.
Figure 5:
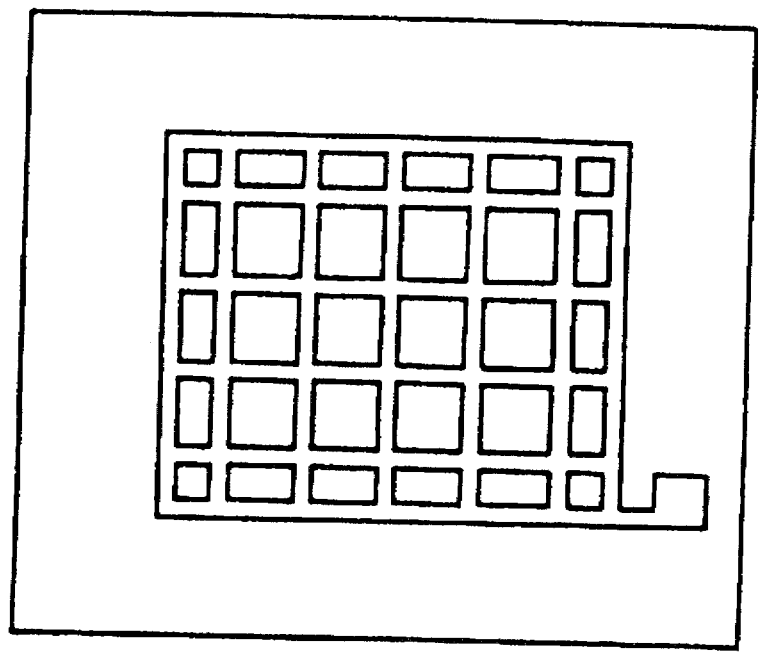
FIG. 5 shows another example of an electrode pattern.

FIGS. 3–5 show examples of patterns for electrodes 13 and 14. In FIG. 3, the whole of a given region has been made into an electrode, while FIG. 4 depicts a comb-like pattern and FIG. 5 shows a grating-type pattern with variations in the area of the grating openings. Thick film formation is convenient for electrodes 13 and 14 as well, and use of this technique enables electrodes with all sorts of patterns to be formed.

The compositions of the pasty substances used in the first embodiment are given in Table 1.

TABLE 1

| Pasty substance comprising p-type semiconductor material particles | | |
|---|---|---|
| vehicle | ethyl cellulose | 7 g |
|  | BCA | 35 g |
|  | α-terpineol | 3 g |
|  | DBP | 2 g |
| solid particle component | CuO | 140 g |
|  | glass powder | 14 g |
| vehicle | ethyl cellulose | 7 g |
|  | BCA | 35 g |
|  | α-terpineol | 35 g |
|  | DBP | 23 g |
| solid particle component | ZnO | 140 g |
|  | glass powder | 14 g |

Figure 6:
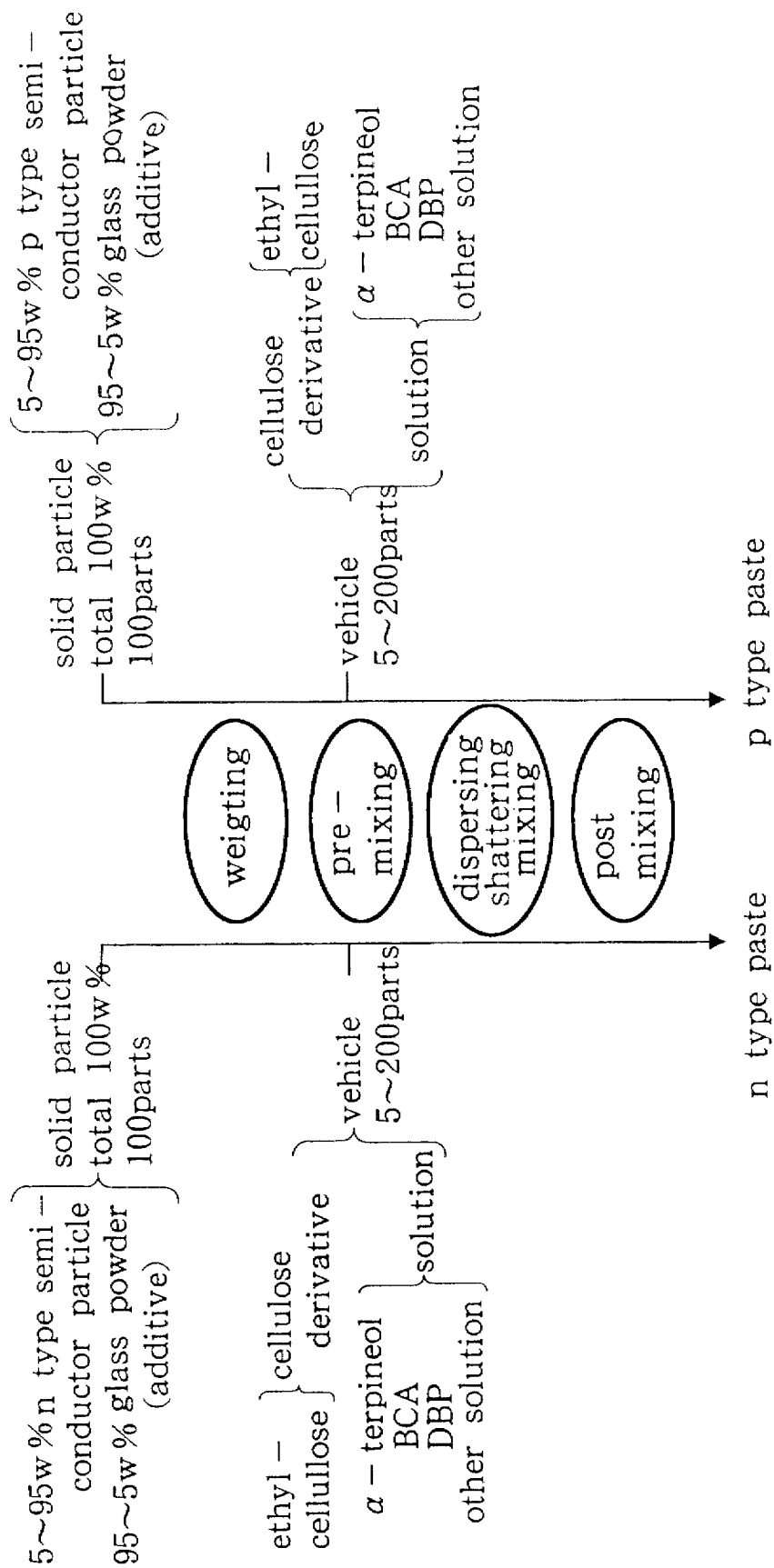
FIG. 6 explains the mix proportions of the pasty substances and the procedures involved in their preparation.

The procedure for preparing the pasty substances is set out in FIG. 6. BCA is Butyl Carbitol acetate. DBP is di-n-butyl phthalate.

Figure 7:
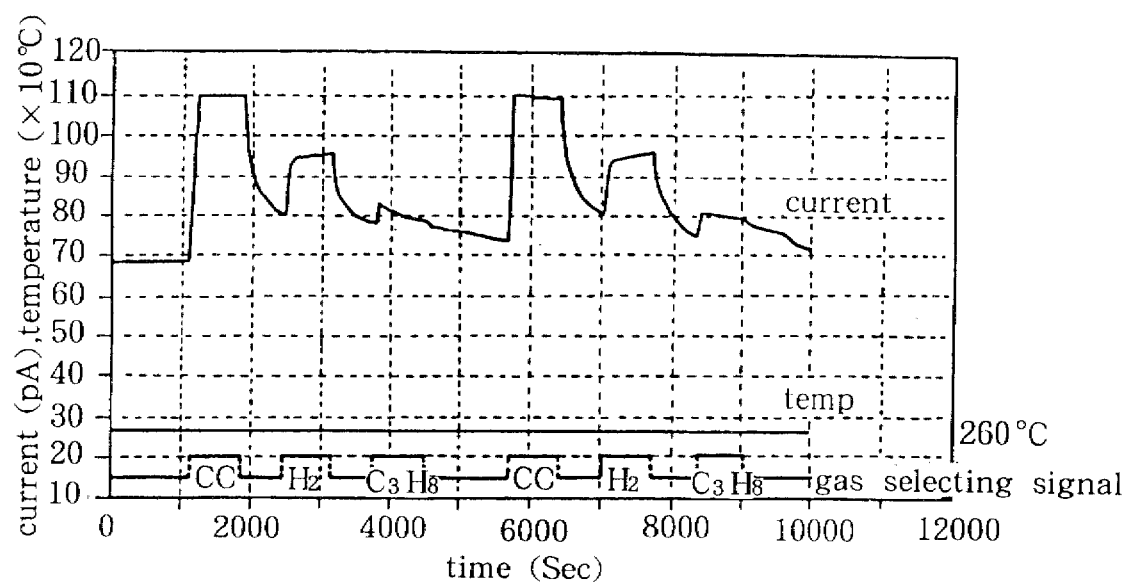
FIG. 7 gives the results of tests of the first embodiment, showing changes in current over a period of time during which a series of different test gases was used.

FIG. 7 gives the results of tests of a gas sensor with the construction shown in FIG. 1, as tested with the circuit shown in FIG. 2, using electrodes of the sort shown in FIG. 4. The horizontal axis in this figure is time, and the figure gives the following information: (i) gas sensor temperature, (ii) the gas changeover signals that show when the test gas was changed over, and (iii) the changes in current with time in response to gas changeover. The units of current are pA and those of temperature are ×10° C. The temperature of the gas sensor was maintained at 260° C., and a DC bias voltage of 0.7 V was applied in the forward direction. The test gases were CO, $H_2$ and $C_3H_8$, at a concentration of 4000 ppm in each case.

It will be seen from FIG. 7 that the sensor is sensitive to each of the test gases. In particular, it is evident that under the conditions employed, sensitivity to CO was excellent.

Second Embodiment

Figure 8A:
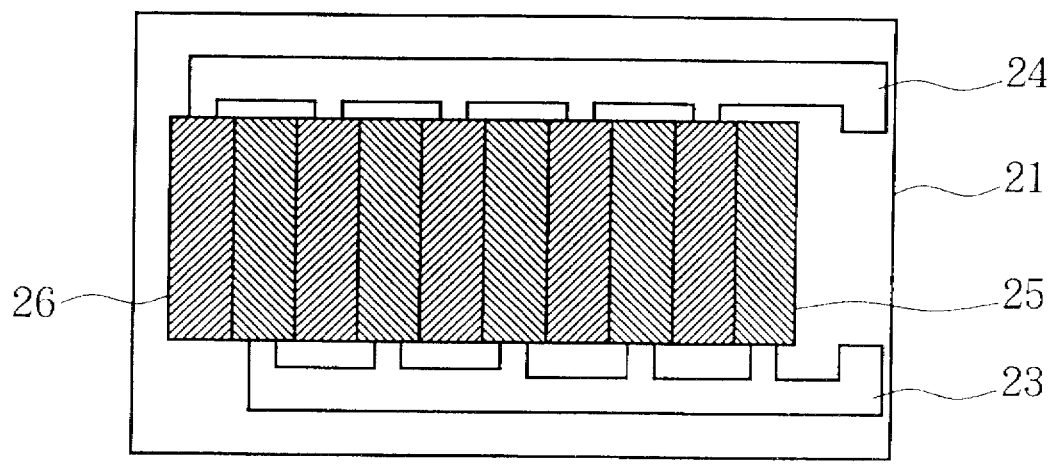
FIG. 8a is a plan view of a second embodiment of this invention.
Figure 8B:
FIG. 8b is the corresponding sectional view.
Figure 9:
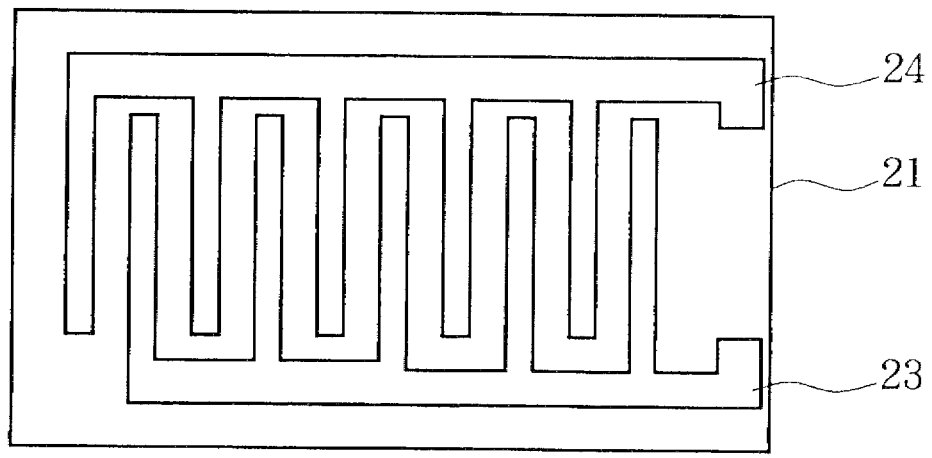
FIG. 9 shows the electrode pattern used in the second embodiment.

FIG. 8a and FIG. 8b show a second embodiment of this invention. FIG. 8a is a plan view and FIG. 8b is a transverse sectional view. FIG. 9 shows the pattern of the electrodes used in this embodiment.

This embodiment differs from the first embodiment in that the two comb-type electrodes 23 and 24 are provided on the surface of one and the same insulating substrate 21, and p-type semiconductor thick film 25 and n-type semiconductor thick film 26 are formed on the same surface in such manner that they are in contact with electrodes 23 and 24, respectively. The two semiconductor thick films 25 and 26 are constituted in such manner that they are in mutual contact and that a gas containing the gas to be detected can be introduced to these contact regions.

The composition of the pasty substances was as given in Table 1 shown above.

A gas sensor with the electrodes shown in FIG. 9 and having the structure shown in FIG. 8a and FIG. 8b was tested in the circuit illustrated in FIG. 2. The results of the tests are given in FIG. 10. The horizontal axis in FIG. 10 is time and the vertical axis shows current and the temperature of the contact regions.

The temperature of the gas sensor was maintained at 260° C. and the bias voltage was 1 V DC in the forward direction. The test gases were CO, $H_2$ and $C_3H_8$, and in each case a concentration of 4000 ppm was employed.

Figure 10:
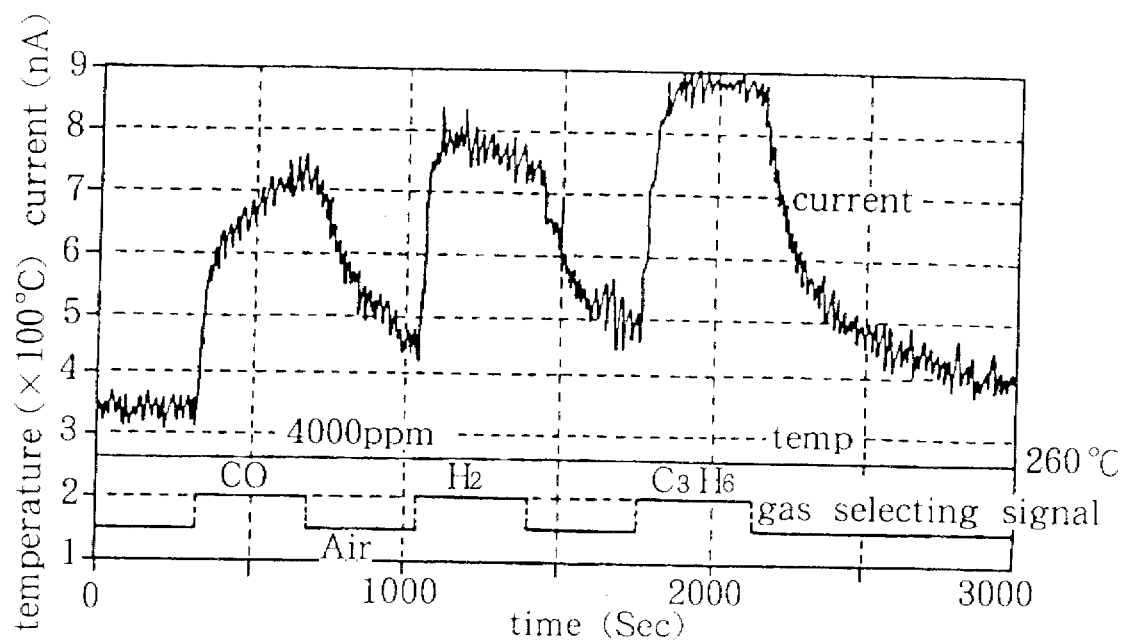
FIG. 10 gives the results of tests of the second embodiment, showing changes in current over a period of time during which a series of different test gases was used.

It will be seen from FIG. 10 that there was considerable sensitivity to each of the test gases.

Third Embodiment

Figure 11A:
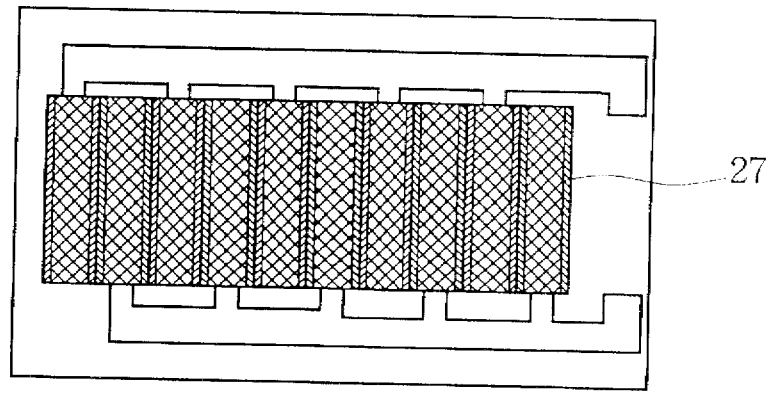
FIG. 11a is a plan view of a partially modified version of the second embodiment.
Figure 11B:
FIG. 11b is the corresponding transverse sectional view.

FIG. 11a and FIG. 11b show the structure of a third embodiment, FIG. 11a being a plan view and FIG. 11b being a transverse sectional view. The structure of this third embodiment should be called a partially modified version of the second embodiment. In this version, protective film 27 has been provided on the surface of p-type semiconductor thick film 25 and n-type semiconductor thick film 26, apart from the p-n contact regions. This protective film 27 excludes gas, and is applied so that gas will come into contact with the p-n contact regions only. The composition of the pasty substances was as given in Table 1 shown above.

Figure 12:
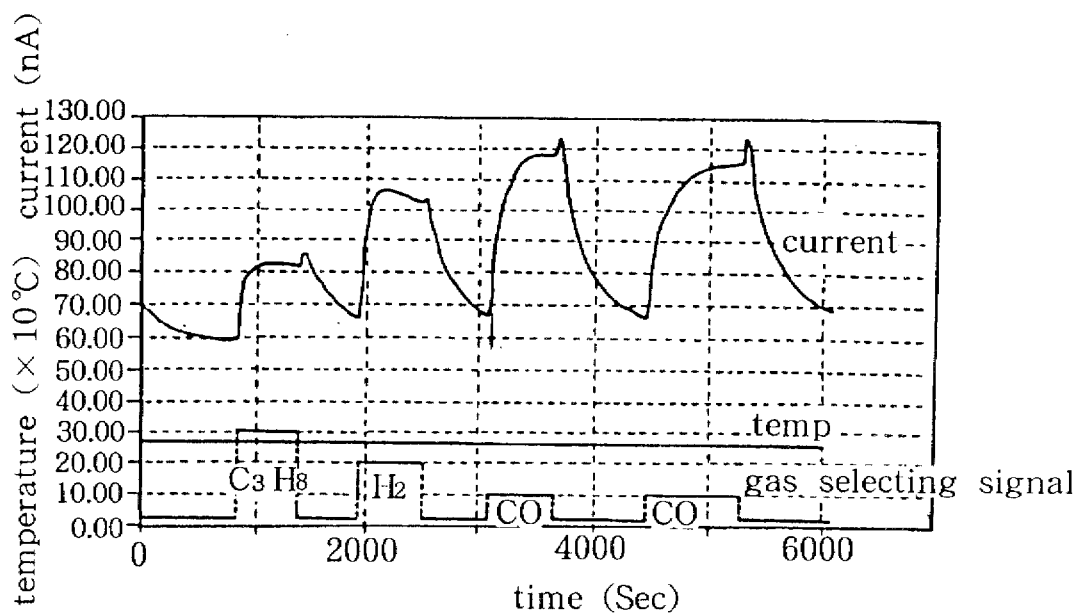
FIG. 12 gives the results of tests of this partially modified version of the second embodiment, showing changes in current over a period of time during which a series of different test gases was used.

The results of tests of this third embodiment are set out in FIG. 12. The horizontal axis of FIG. 12 is time and the vertical axis shows change in current and the temperature of the contact regions. Accordingly, the figure gives the following information: (i) gas sensor temperature, (ii) the gas changeover signals that show when the test gas was changed over, and (iii) the changes in current in response to gas changeover. The conditions employed for these tests were identical to those used in the tests of the second embodiment, the results of which are given in FIG. 10 above. Namely, the gas sensor temperature was 260° C., a forward bias voltage of 1 V was used, and the test gases were CO, $H_2$ and $C_3H_8$ at a concentration of 4000 ppm in each case.

It will be seen from these results that compared with the second embodiment, this third embodiment gave greater selectivity for CO gas and a much more pronounced change in current at the contact regions.

Fourth and Fifth Embodiments

Figure 13:
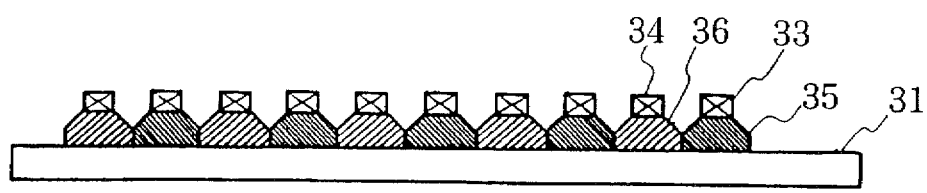
FIG. 13 is a transverse sectional view of a fourth embodiment of this invention.
Figure 14:
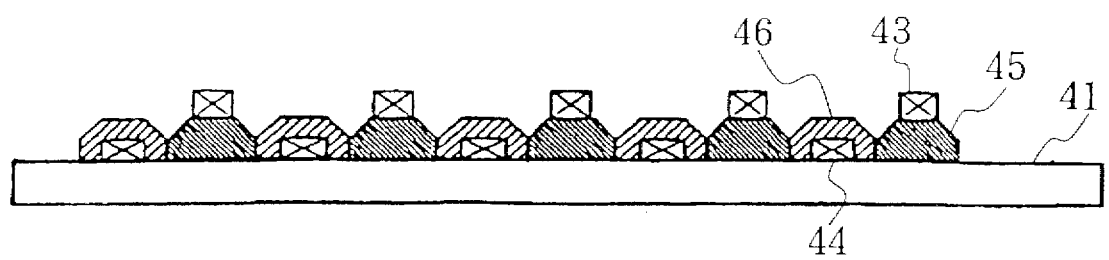
FIG. 14 is a transverse sectional view of a fifth embodiment of this invention.

FIG. 13 is a transverse sectional view of a fourth embodiment of this invention. FIG. 14 is a transverse sectional view of a fifth embodiment. These embodiments are examples where the positional relation of the electrodes and semiconductor thick films relative to the substrate is different from that of the second embodiment. In the fourth embodiment shown in FIG. 13, p-type semiconductor thick films 35 and n-type semiconductor thick films 36 are formed directly on the surface of substrate 31, and electrodes 33 and 34 are provided respectively on the surfaces of these. In the fourth embodiment shown in FIG. 14, n-side electrode 44 and p-type semiconductor thick films 45 are formed on the surface of substrate 41, while n-type semiconductor thick films 46 and p-side electrode 43 are formed respectively on the surfaces of these. The electrodes and semiconductor thick films can also be formed with the arrangement of p-type and n-type shown in this example reversed.

Sixth Embodiment

Figure 15:
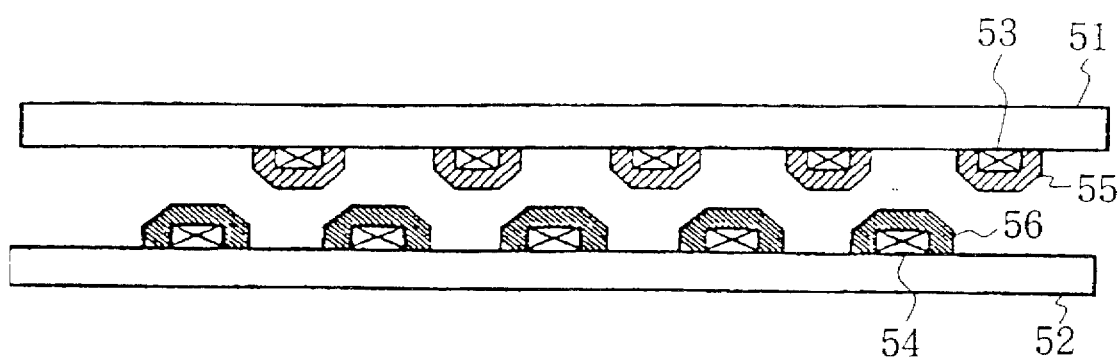
FIG. 15 is a transverse sectional view of a sixth embodiment of this invention, and shows the situation prior to assembly as a gas sensor.
Figure 16:
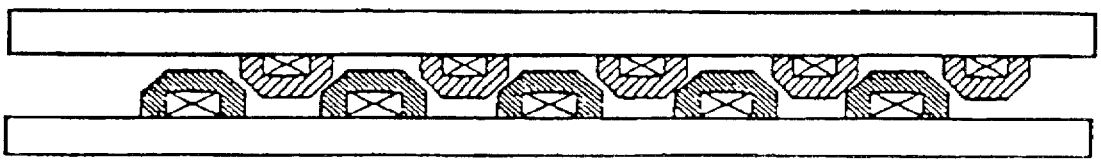
FIG. 16 is a transverse sectional view showing the situation after assembly of the sixth embodiment.

FIG. 15 and FIG. 16 are both transverse sectional views of a sixth embodiment of this invention, with FIG. 15 showing the situation prior to assembly as a gas sensor, and FIG. 16 showing the situation after assembly. The distinguishing feature of this embodiment is that the two kinds of semiconductor thick film remain discrete in the sense of not forming a single plane, and that the p-type semiconductor thick films and n-type semiconductor thick films are brought into contact with a stagger equivalent to half the spacing pitch. Namely, comb-type electrode 53 is provided on the surface of substrate 51, and p-type semiconductor thick film 55 is formed in contact with this electrode 53. Likewise, comb-type electrode 54 and in contact with this, n-type semiconductor thick film 56, are provided on the surface of substrate 52. As shown in FIG. 15, p-type semiconductor thick film 55 and n-type semiconductor thick film 56 are then brought into contact after being staggered by half the spacing pitch. It is desirable for p-type semiconductor thick film 55 and n-type semiconductor thick film 56 to be provided also on the sides of electrodes 53 and 54, respectively. This ensures that there is a good contact area and improves the gas distribution.

Figure 17:
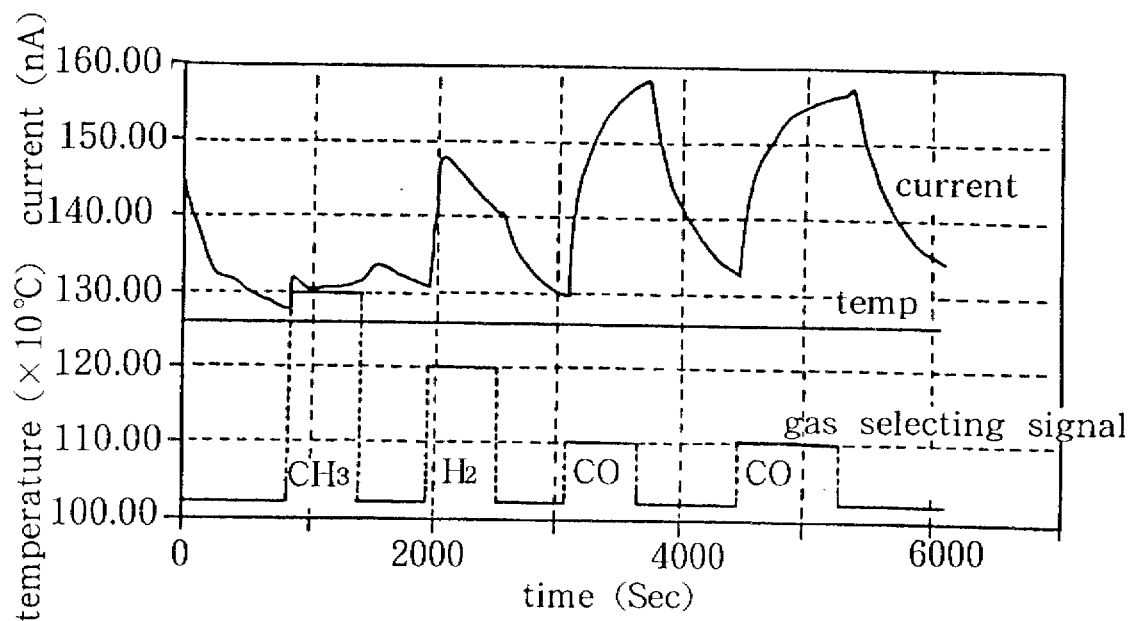
FIG. 17 gives the results of tests of the fifth embodiment, showing changes in current over a period of time during which a series of different test gases was used.

FIG. 17 gives the results of tests of this sixth embodiment. Namely, a gas sensor with the structure shown in FIG. 16 was tested in the circuit depicted in FIG. 2. The horizontal axis of FIG. 17 is time and the vertical axis gives-current and the temperature of the contact regions. The timing of the gas changeover signal is also shown in this figure. The composition of the pasty substances used in this sixth embodiment was as shown in Table 1 above. The conditions employed for these tests were identical to those used in the tests of the second embodiment, the results of which are given in FIG. 10 above. Namely, the gas sensor temperature was 260° C., a forward bias voltage of 1 V was used, and the test gases were CO, $H_2$ and $C_3H_8$ at a concentration of 4000 ppm in each case.

From these results it will be seen that with this structure, the absolute value of the current increases. This is thought to be because the surface area of the contact regions has been substantially increased.

Figure 18:
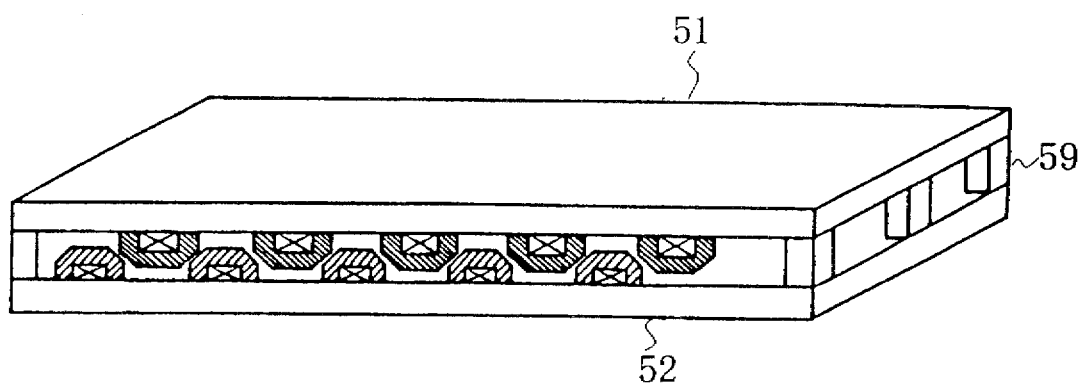
FIG. 18 is a perspective view of a partially modified version of the sixth embodiment.
Figure 19:
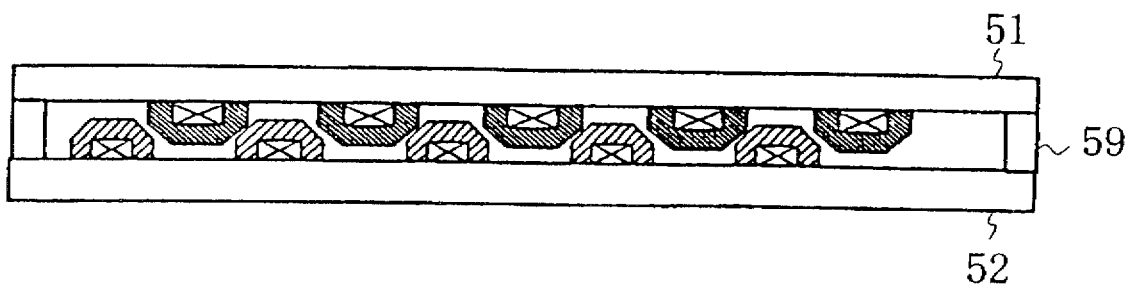
FIG. 19 is a transverse sectional view of the same gas sensor as in FIG. 18.

FIG. 18 and FIG. 19 show a partially modified version of the sixth embodiment, FIG. 18 being a perspective view and FIG. 19 being a transverse sectional view. In this version, glass powder has been melted and deposited in order to pressure-bond the two substrates 51 and 52 mechanically. Deposits 59 are formed at specific points only, so that the flow of gas is not impeded, and are stable once the mechanical pressure-bonding has been carried out. Manufacturing yield is improved by means of this structure.

Seventh Embodiment

Figure 20:
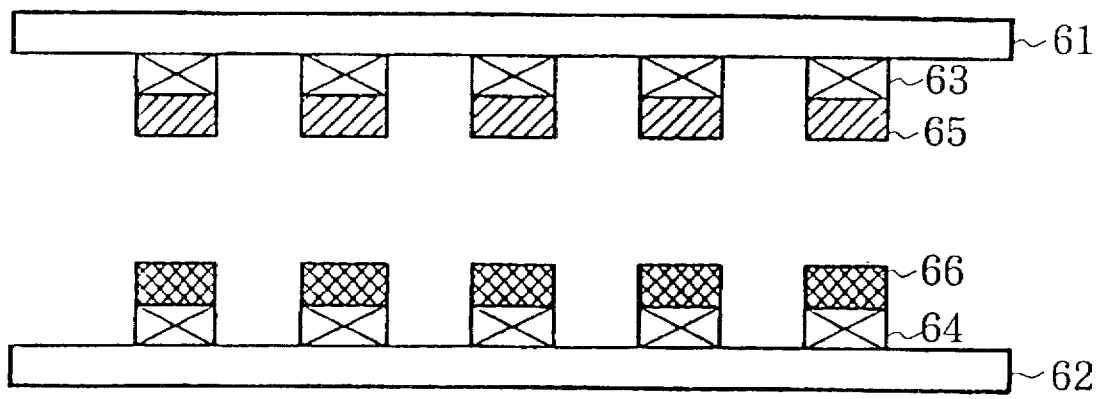
FIG. 20 is a transverse sectional view of a seventh embodiment of this invention, and shows the situation prior to assembly as a gas sensor.
Figure 21:
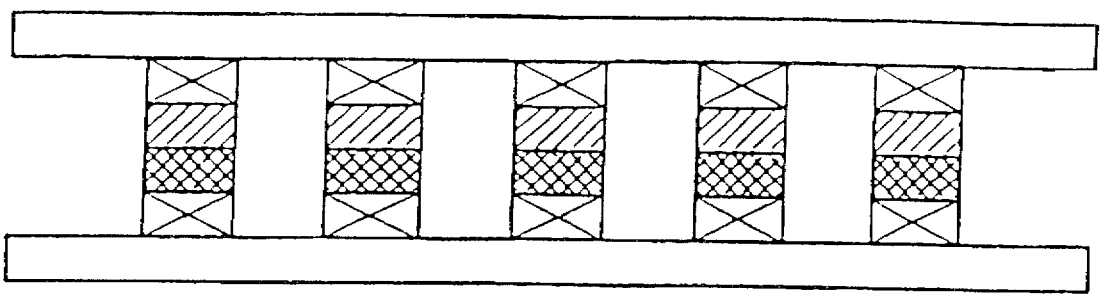
FIG. 21 is a transverse sectional view showing the situation after assembly of the seventh embodiment.

FIG. 20 and FIG. 21 are transverse sectional views of a seventh embodiment of this invention, with FIG. 20 showing the situation prior to assembly as a gas sensor, and FIG. 21 showing the situation after assembly.

This embodiment differs from the sixth embodiment in that the tops of the p-type semiconductor thick films and the n-type semiconductor thick films are in contact with each other, and have not been staggered. That is to say, comb-type electrode 63 is provided on the surface of substrate 61, and p-type semiconductor thick films 65 are formed in contact with this electrode 63. Likewise, comb-type electrode 64 and in contact with this, n-type semiconductor thick films 66, are provided on the surface of substrate 62. P-type semiconductor thick films 65 and n-type semiconductor thick films 66 are arranged in such manner that they face one another. Given this constitution, fabrication tolerances are large and so lower manufacturing cost is possible. It may be noted that although in FIG. 19 and FIG. 20, no semiconductor thick films have been provided on the sides of electrodes 63 and 64, these parts may be covered with semiconductor thick films in similar manner to the sixth embodiment.

Figure 22:
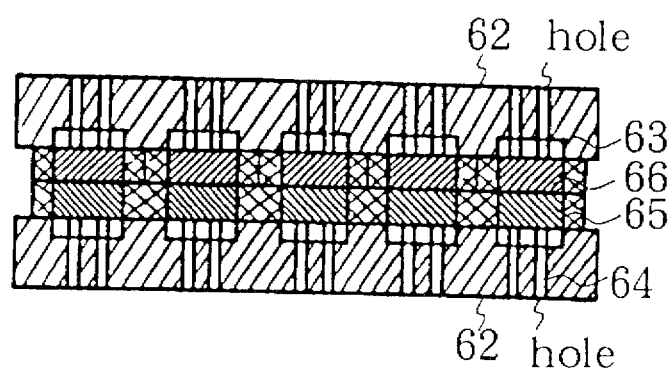
FIG. 22 shows a modified version of part of the structure of the seventh embodiment.

FIG. 22 is a sectional view of a partially modified version of the seventh embodiment. In this version, at least part of each of substrates 61 and 62, electrodes 63 and 64, p-type semiconductor thick film 65 and n-type semiconductor thick film 66 are formed so as to be porous, so that the gas to be tested can pass through the porous parts and reach the contact regions.

Eighth Embodiment

Figure 23:
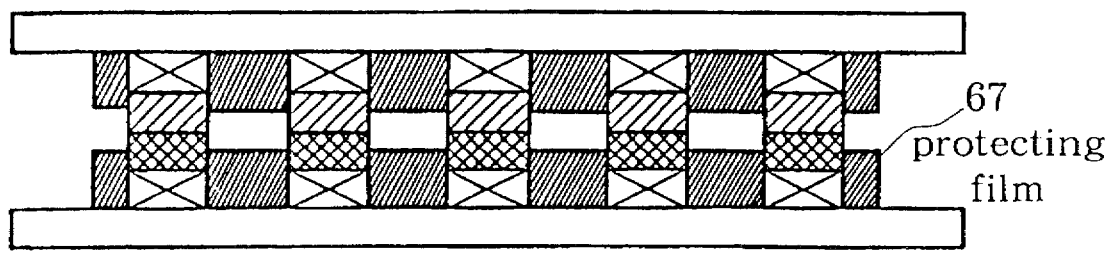
FIG. 23 shows the structure of an eighth embodiment.

FIG. 23 is a transverse sectional view of an eighth embodiment. This is a partially modified version of the seventh embodiment, with protective film 67 being provided so as to cover electrodes 63 and 64 and the two semiconductor thick films 65 and 66, apart from the contact regions between p-type semiconductor thick film 65 and n-type semiconductor thick film 66. This protective film 67 excludes gas, and is applied so that gas will come into contact with the pn contact regions only. This gives a further improvement in sensitivity to the gas being tested.

Figure 24:
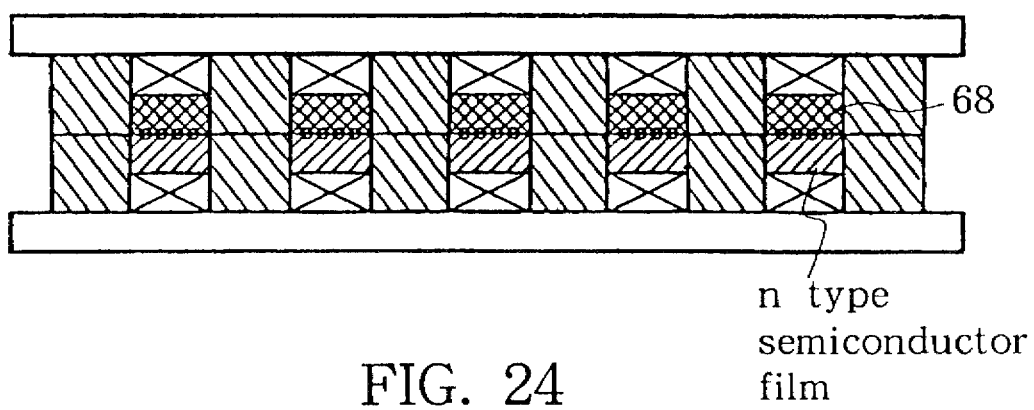
FIG. 24 shows a partially modified version of FIG. 23.

FIG. 24 is a further partially modified version of the eighth embodiment shown in FIG. 23. In the version shown in FIG. 23, the sides of the p-n contact regions were exposed so that gas could be introduced into these regions. As opposed to this, the version shown in FIG. 24 is constructed so that the p-n contact regions are completely covered by protective film 67 (i.e., this protective film covers their sides as well) and gas is actively introduced to the p-n contact regions by the provision of gas ventilation holes 68 in these regions. This version gives a further improvement in sensitivity to the test gas.

Ninth Embodiment

Figure 25:
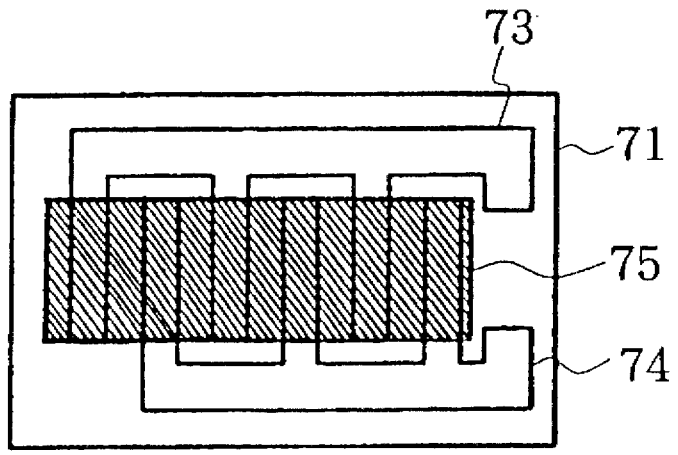
FIG. 25 is a plan view of a ninth embodiment of this invention.
Figure 26:
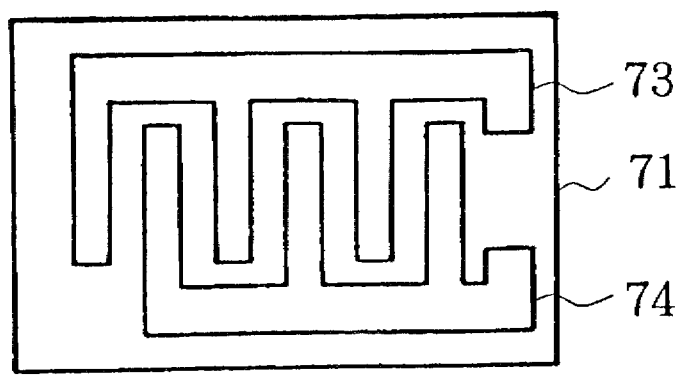
FIG. 26 is a plan view of the electrode patterns of the ninth embodiment.

FIG. 25 is a plan view of a ninth embodiment of this invention, and FIG. 26 is a plan view showing the electrode pattern used in this ninth embodiment.

This embodiment has electrodes 73 and 74 on the surface of one and the same insulating substrate 71, and its distinguishing feature is that mixed pn semiconductor thick film 75 comprising particles of a p-type semiconductor material and particles of an n-type semiconductor material which have been kneaded together and formed into a solid, has been provided and is connected to these electrodes 73 and 74.

Figure 27:
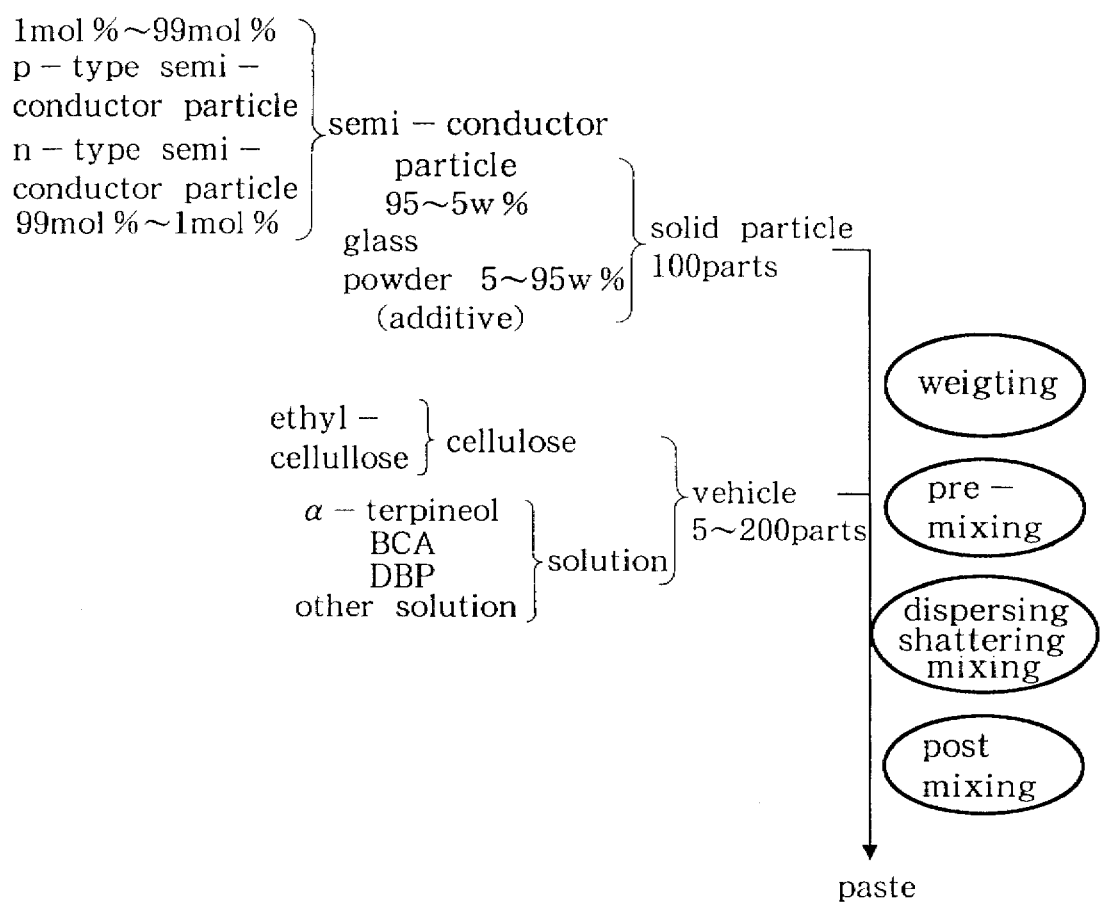
FIG. 27 explains the mix proportions of the pasty substances and the procedures involved in their preparation.

To manufacture this gas sensor, two comb-type electrodes 73 and 74 are formed (for example, as shown in FIG. 26) on the surface of substrate 71, and a pasty substance comprising homogeneously kneaded particles based on a p-type semiconductor material and particles based on an n-type semiconductor material is coated or printed so as to be in contact with both of these electrodes 73 and 74, and is then fired. The procedure for preparing this pasty substance is set out in FIG. 27.

TABLE 2

| vehicle | |
|---|---|
| ethyl cellulose | 7 g |
| BCA | 35 g |
| α-terpineol | 35 g |
| DBP | 23 g |
| solid particle component | |
| CuO | 70 g |
| ZnO | 70 g |
| glass powder | 14 g |

Figure 28:
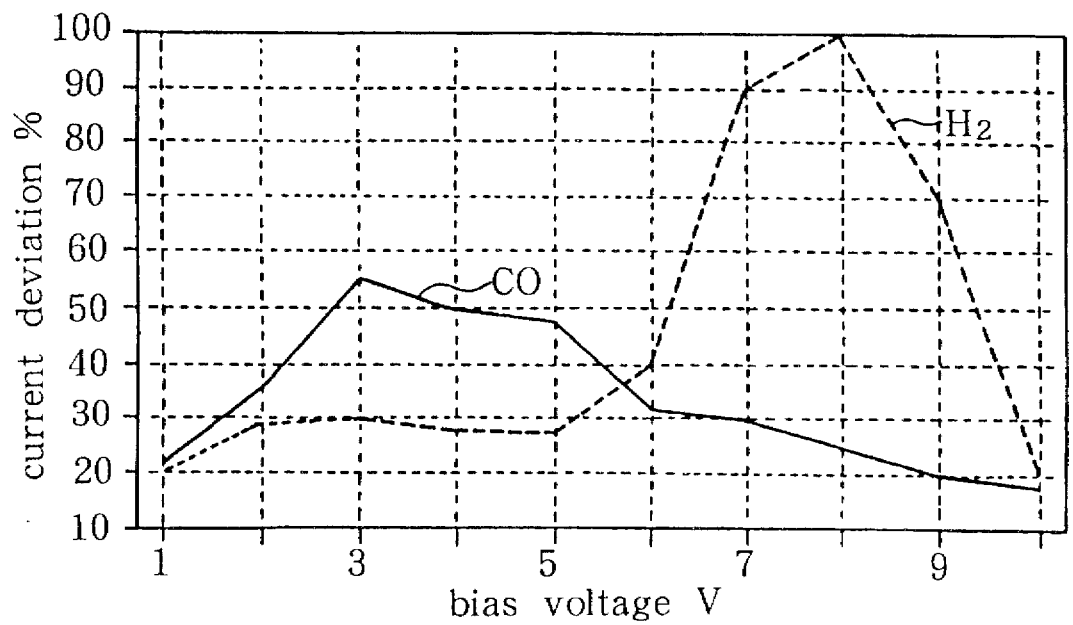
FIG. 28 gives the results of tests of the ninth embodiment, the horizontal axis showing the bias voltage and the vertical axis showing the percentage change in current.

The results of tests of the gas sensor shown in FIG. 25 using the electrode pattern shown in FIG. 26 are given in FIG. 28. The horizontal axis is the bias voltage (V) and the vertical axis is the percentage change in current (%). The composition of the pasty substance is as shown in Table 2. For the duration of the tests, the junction region was maintained at 260° C. Both the test gases CO and $H_2$ were used at 4000 ppm in air. As will be seen from FIG. 28, there was sensitivity to CO in the vicinity of a bias voltage of 3 V and sensitivity to $H_2$ in the vicinity of a bias voltage of 8 V. In other words, it is evident that bias voltage gives gas type selectivity.

Figure 29:
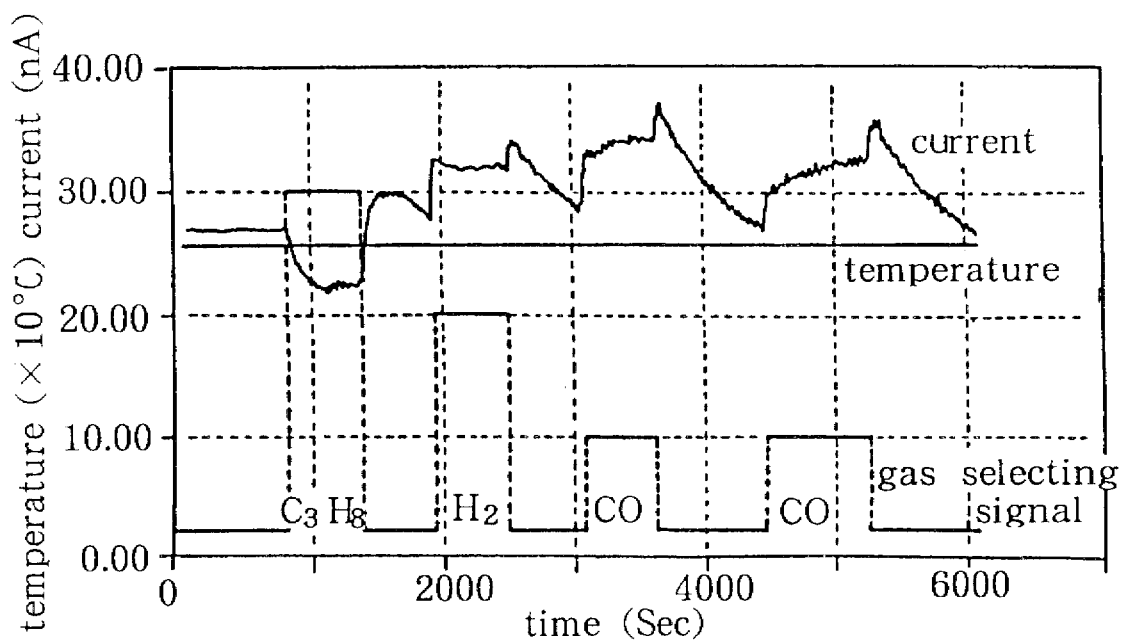
FIG. 29 gives the results of tests of the ninth embodiment, showing changes in current over a period of time during which a series of different test gases was used.

The gas sensor shown in FIG. 25 having the electrode pattern depicted in FIG. 26 was also fabricated using a different pasty substance, the composition of which had been altered as shown in Table 3. The results of tests of this gas sensor are set out in FIG. 29. The horizontal axis of FIG. 29 is time and the vertical axis gives current and the temperature of the contact region. For the duration of the tests, the junction region was maintained at 260° C. All the test gases (CO, $H_2$ and $C_3H_8$) were at 4000 ppm in air.

TABLE 3

| vehicle | |
|---|---|
| ethyl cellulose | 7 g |
| BCA | 35 g |
| α-terpineol | 35 g |
| DBP | 23 g |
| solid particle component | |
| CuO | 14 g |
| ZnO | 130 g |
| glass powder | 14 g |

The results shown in FIG. 29 indicate that at a bias voltage of 5 V, current decreased when $C_3H_8$ was detected and increased when $H_2$ and CO were detected. In other words, it will be seen that the polarity of the sensitivity reversed. The change in current in the detection of CO is greater than the change for $H_2$. Comparison with the results shown in FIG. 28 makes it clear that the characteristics of the sensor can be adjusted by altering the mixing ratio of CuO and ZnO. These results show that gas properties or type can be discriminated by the direction of current change: in other words, by whether current change is positive or negative. Regarding this phenomenon, tests carried out by the inventors have shown that the kind of gas which can be discriminated varies according to composition of the materials, distance between electrodes, bias voltage and heating temperature.

Figure 30:
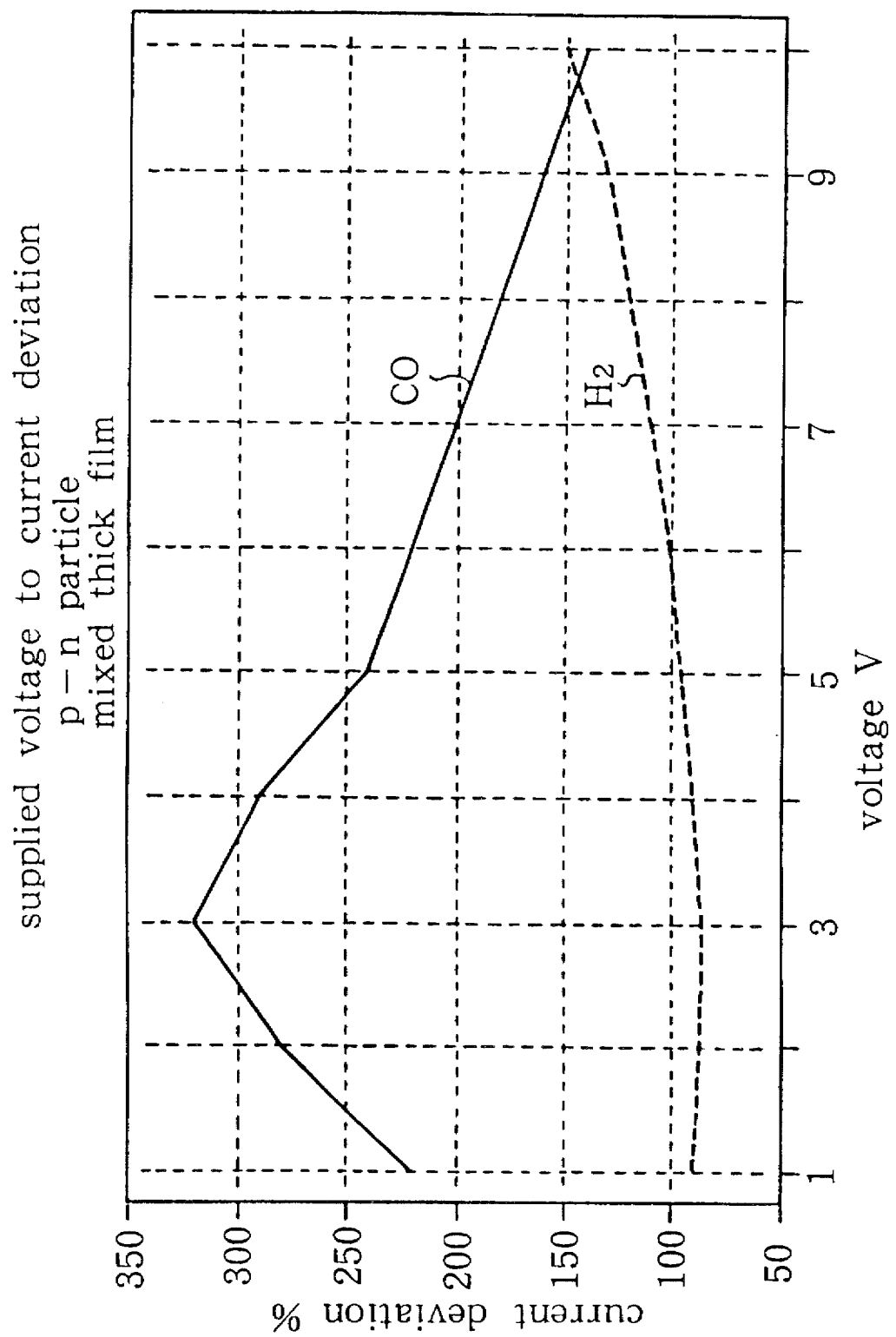
FIG. 30 gives the results of the same tests as those upon which FIG. 28 was based, but with a different distance between electrodes.

The results of a further set of tests are shown in FIG. 30. In this case, instead of altering the mixing ratio of the pasty substance, the gap between the electrodes was changed. The sensor that gave the test results shown in FIG. 28 had an inter-electrode distance (i.e., the distance between the positive and negative electrodes) of 700 μm, and this was changed to 130 μm.

Figure 31:
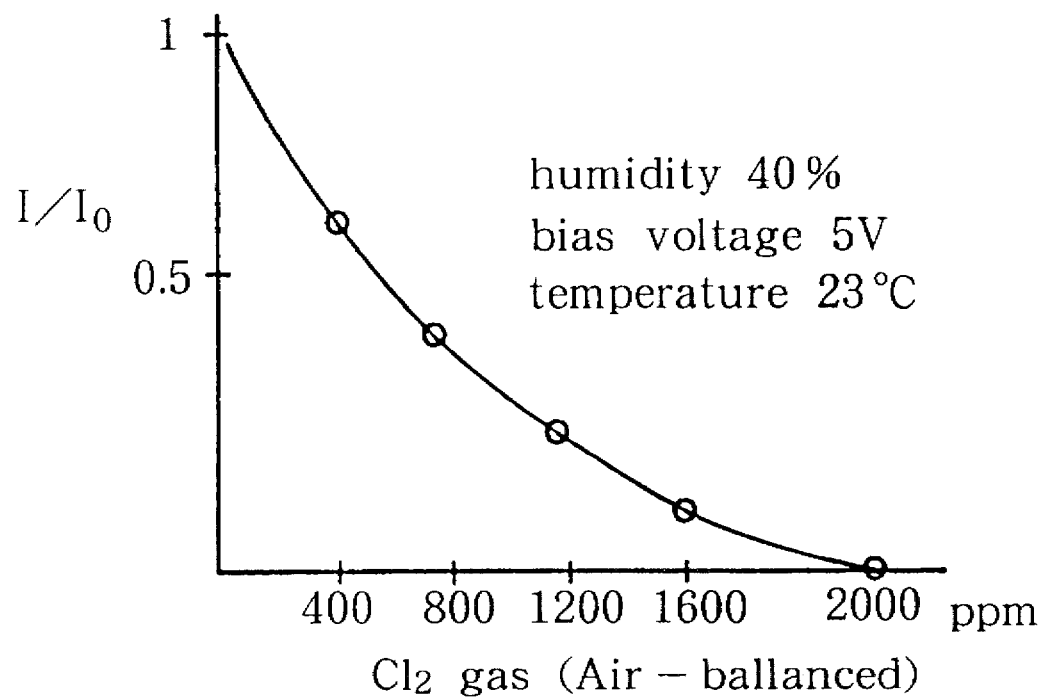
FIG. 31 gives the results of tests of the ninth embodiment, showing $Cl_2$ gas concentration along the horizontal axis and percentage change in current along the vertical axis.

FIG. 31 gives the results of a $Cl_2$ gas sensitivity test of a gas sensor of the sort shown in FIG. 25 and having the electrode pattern shown in FIG. 26. The pasty substance in this case had a composition in accordance with Table 2, except that SiC was used instead of CuO. This test was carried out in the air at a temperature of 23° C. and a humidity of 40%, with a bias voltage of 5 V. The current change ratio in response to the test gas is shown along the vertical axis in FIG. 31, and the concentration of $Cl_2$ gas in air (units: ppm) is shown along the horizontal axis.

With gas sensors of this sort, no rectification behaviour is exhibited between electrodes 73 and 74. However, when such sensors were actually fabricated, changes in resistivity in the presence of a gas were observed, and it was confirmed that the sensors operate with alternating current. This is thought to be because the p-type semiconductor and the n-type semiconductor are intermixed in the particulate state, and because p-n contacts are formed between these respective particles.

Figure 32:
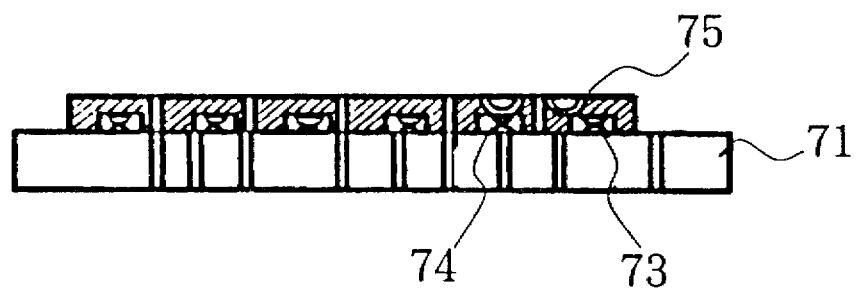
FIG. 32 is a sectional view showing a partially modified version of the ninth embodiment.

FIG. 32 is a sectional view of a partially modified version of the ninth embodiment. In this version, a porous ceramic is used as substrate 71, so that gases pass through substrate 71. In conjunction with this, pn semiconductor thick film 75 can also be made porous. In addition, electrodes 73 and 74 can also be made porous. It is also feasible to make only pn semiconductor thick film 75 porous.

Figure 33:
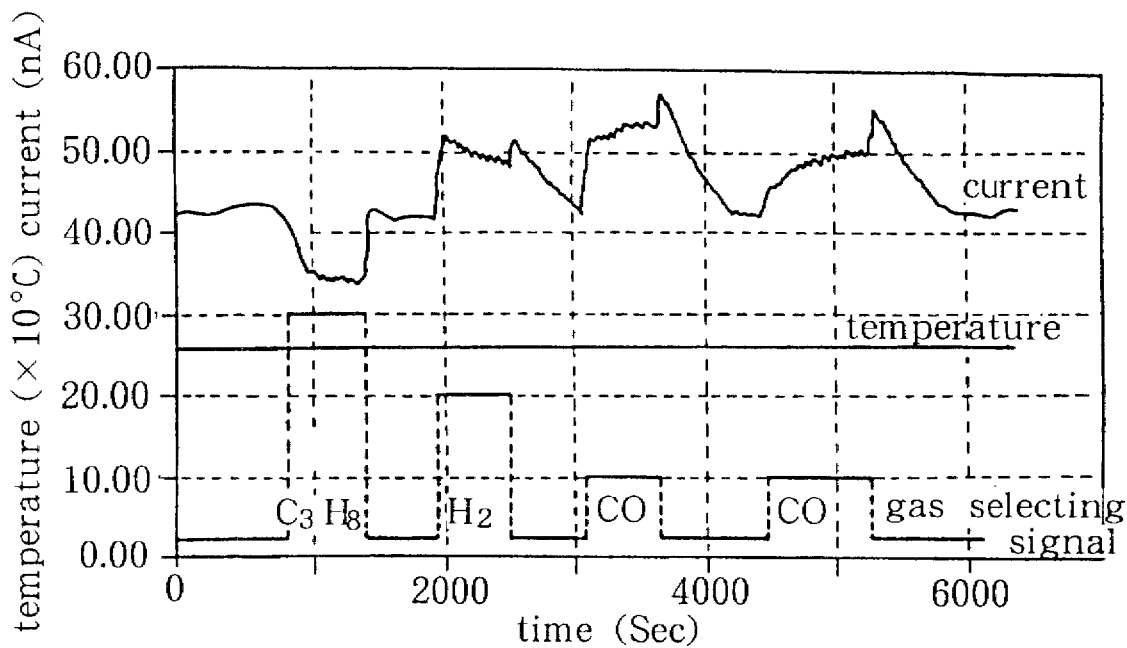
FIG. 33 gives the results of another test of a gas sensor constructed in accordance with the first embodiment, showing changes in current over a period of time during which a series of different test gases was used.

FIG. 33 gives the results of tests of a gas sensor fabricated with the structure shown in FIG. 32 and using a pasty substance with the composition set out in Table 3. The horizontal axis in FIG. 33 is time and the vertical axis gives current and the temperature of the contact region. For the duration of the tests, the junction region was maintained at 260° C. The bias voltage was 5 V. All of the test gases (CO, $H_2$ and $C_3H_8$) were used at 4000 ppm in air.

It will be seen that with this version, current values are larger and sensitivity higher for all the test gases.

Other Embodiments

Figure 34:
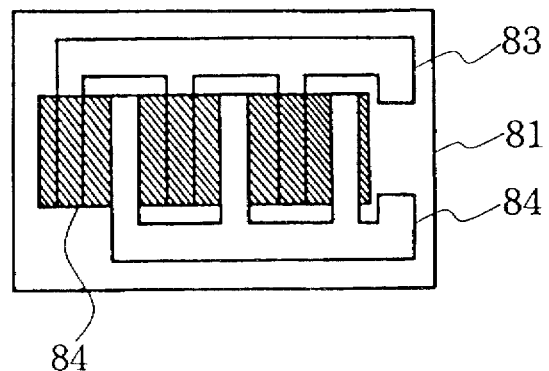
FIG. 34 is a plan view of a tenth embodiment of this invention.
Figure 35:
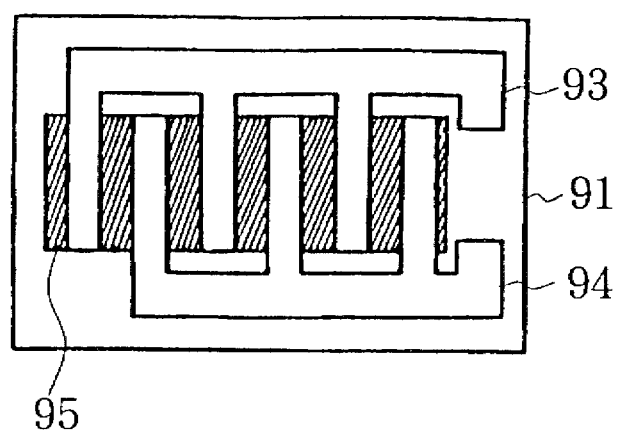
FIG. 35 is a plan view of an eleventh embodiment of this invention.

FIG. 34 is a plan view of a tenth embodiment of this invention, and FIG. 35 is a plan view of an eleventh embodiment. The arrangement of the electrodes in these embodiments is different from that in the ninth embodiment. In the embodiment shown in FIG. 34, one of the electrodes is provided on the surface of the semiconductor thick film. In other words, comb-type electrode 83 is provided on the surface of substrate 81, and mixed pn semiconductor thick film 85 comprising particles of a p-type semiconductor material and particles of an n-type semiconductor material which have been kneaded together and formed into a solid, is provided so as to be in contact with this electrode 83. Comb-type electrode 84 is then provided on the surface of this mixed pn semiconductor thick film 85.

In the embodiment shown in FIG. 35, both of the two electrodes are provided on the surface of the semiconductor thick film. In other words, mixed pn semiconductor thick film 95 is provided on the surface of substrate 91, and comb-type electrodes 93 and 94 are formed on the surface of this.

Figure 36:
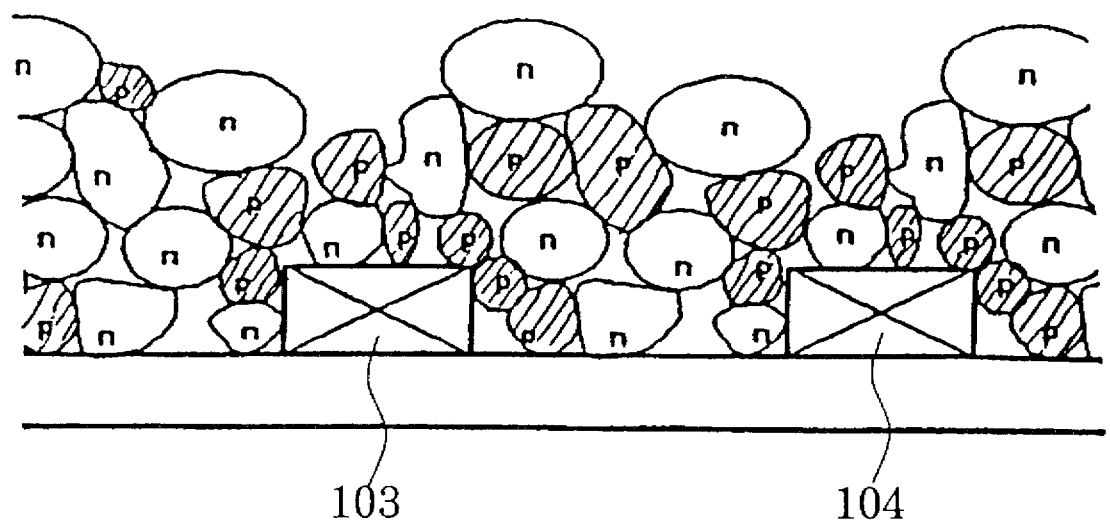
FIG. 36 clarifies the microstructure of a mixed pn semiconductor thick film.

FIG. 36 clarifies the microstructure of a mixed pn semiconductor thick film.

In the ninth, tenth and eleventh embodiments described above, the p-type semiconductor and the n-type semiconductor are not formed separately: instead, the two types of particles are intermixed. For this reason, as shown in FIG. 36, both p-type semiconductor particles and n-type semiconductor particles are in contact with opposing electrodes 103 and 104.

Figure 37:
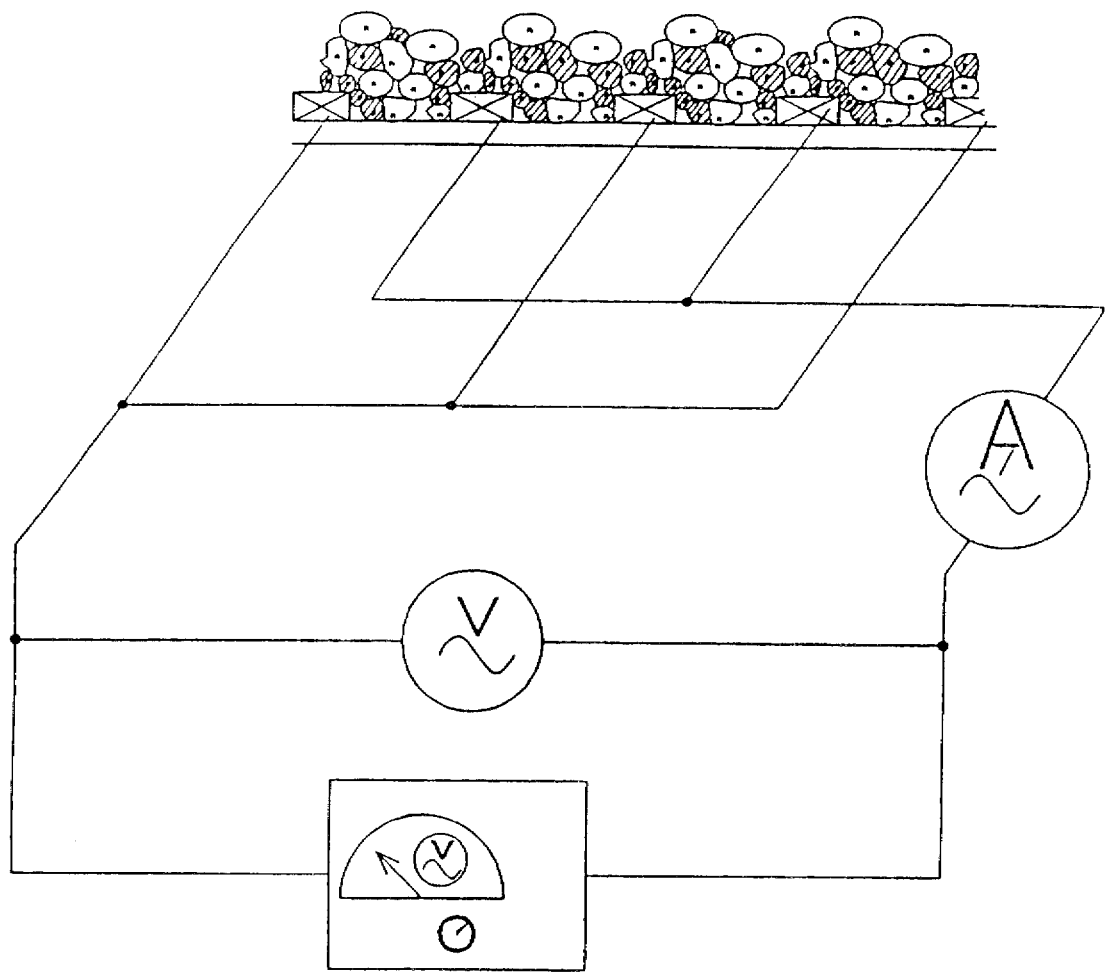
FIG. 37 is a wiring diagram showing an example of AC being applied to a mixed pn semiconductor thick film.

FIG. 37 shows an example of an alternating current being applied to a mixed semiconductor thick film comprising p-type semiconductor particles and n-type semiconductor particles with p-n contacts of the sort shown in FIG. 36. A target gas can be detected by monitoring for changes in current in a circuit of this sort. Because an AC voltage can be applied as the power supply or bias voltage, there is the advantage that no rectifying device is required, since a commercial power supply can be used either directly or after conversion by a transformer. Another advantage is that since processing of the detection signal involves dealing with an AC signal from which any DC components have been removed by a coupling capacitor, it is easy to utilize an amplifier or a noise elimination circuit, with substantial improvement in sensitivity.

AC operation is also possible in cases where p-type semiconductors and n-type semiconductors have been provided separately. An example of a circuit for this type of AC operation is given in FIG. 38. The equivalent circuit is shown in FIG. 39.

Figure 38:
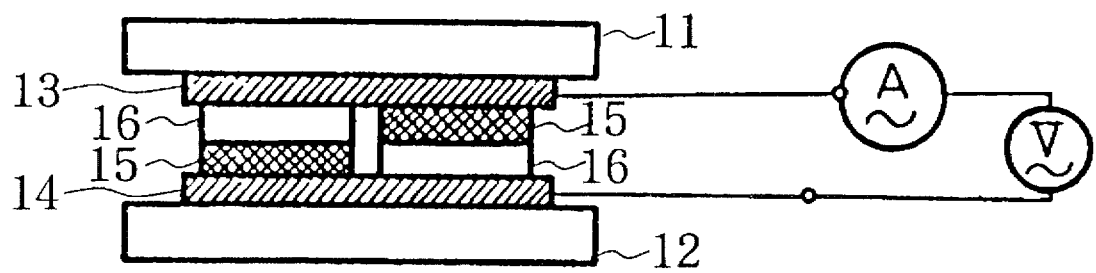
FIG. 38 gives an example of AC operation where separate p and n oxide semiconductors have been provided.
Figure 39:
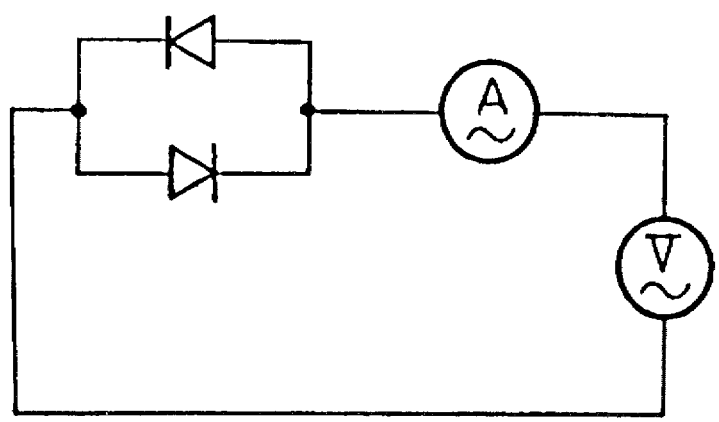
FIG. 39 shows the equivalent circuit.

The example of sensor structure shown in FIG. 38 is a partially modified version of the first embodiment. Here, electrodes 13 and 14 have been provided on substrates 11 and 12 respectively, and p-type semiconductor thick films 15 and n-type semiconductor thick films 16 are provided on both of these substrates 11 and 12. Accordingly, this modified version is equivalent to two of the first embodiment structures connected in parallel in opposite directions, and is therefore capable of AC operation. Operation using an alternating current will provide the same advantages as those outlined above.

Figure 40:
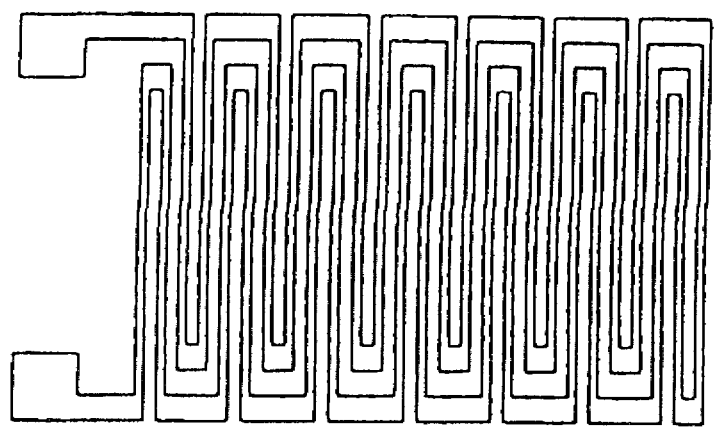
FIG. 40 shows an example of a heater pattern.

FIG. 40 shows an example of a heater pattern. In order to operate, a semiconductor-based gas sensor has to be heated. A sensor may be constructed in such manner that it is heated from the back of the substrate, using a heater with the pattern depicted in FIG. 40, for example.

Figure 41:
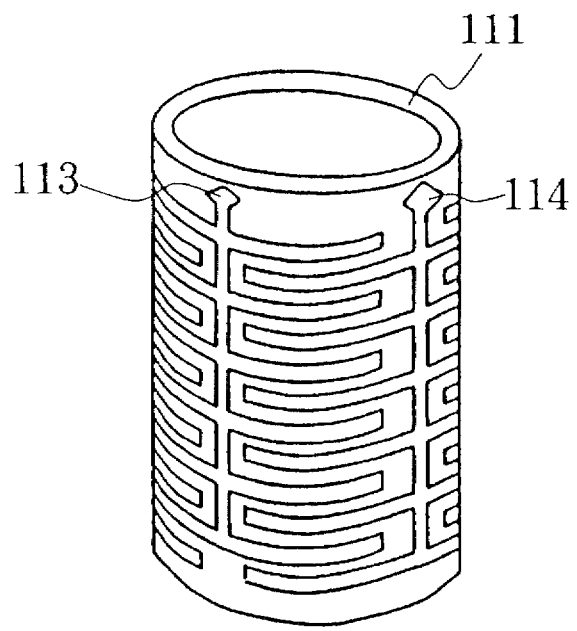
FIG. 41 is a perspective view of a cylindrical substrate and electrodes.
Figure 42:
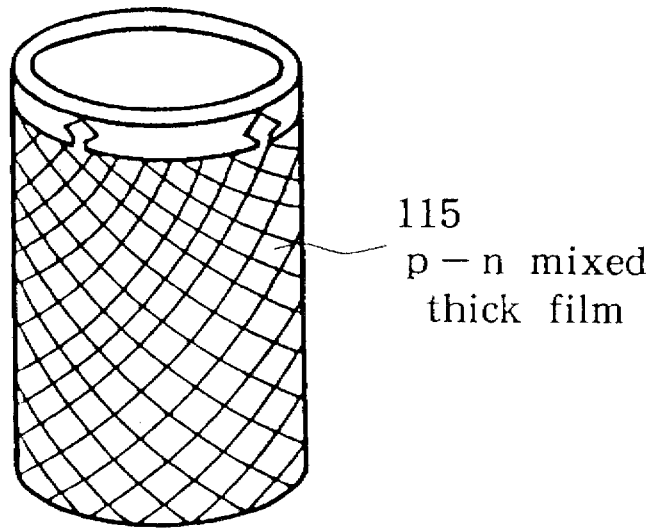
FIG. 42 is a perspective view of an example where a mixed pn semiconductor thick film has been provided on a cylindrical substrate and electrodes.

FIG. 41 shows an example of the shape of a substrate and electrodes. Although the explanations of the foregoing embodiments have dealt with cases in which flat plates have been employed as the substrates, it is also feasible to use a cylindrical substrate 111 and to provide electrodes 113 and 114 on its surface. In this case as well, as shown in FIG. 42, a mixed pn semiconductor thick film 115 may be provided on the surface of electrodes 113 and 114. Alternatively, at least one of electrodes 113 and 114 may be provided on the surface of a mixed pn semiconductor thick film. When the substrate is cylindrical, it will be easier to form the thick film if spray coating is used instead of coating or printing.

Figure 43:
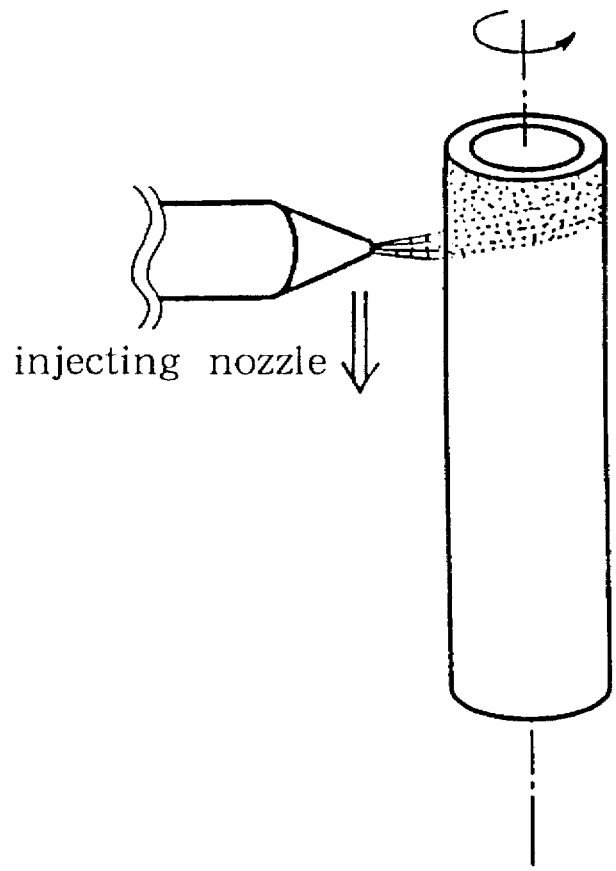
FIG. 43 clarifies the blowing of mixed pn semiconductor material particles onto a cylindrical substrate by spray coating.

As is shown in FIG. 43, thick films can be fabricated by blowing particles of p or n semiconductor materials against a cylindrical substrate which is being rotated about its centre axis, and moving the spray coating nozzle along the substrate axis. It may be pointed out that a detailed account of spray coating is given in:

Citation 6: "Survey of the Latest Surface Treatment Technology", Chapter 4, "Spray Coating". Published by Industrial Technology Service Centre, 21st Dec. 1987.

Citation 7: "Fine Ceramics Handbook," Chapter 8. Compiled by Fine Ceramics Laboratory, MITI. Published by OHM-Sha.

Figure 44:
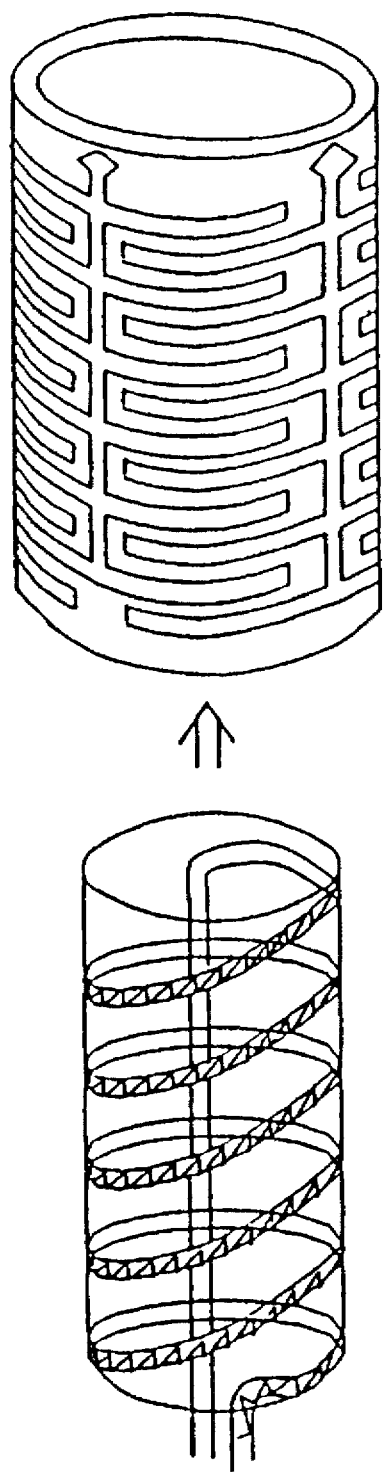
FIG. 44 shows an example of a heater for a cylindrical substrate.
Figure 45:
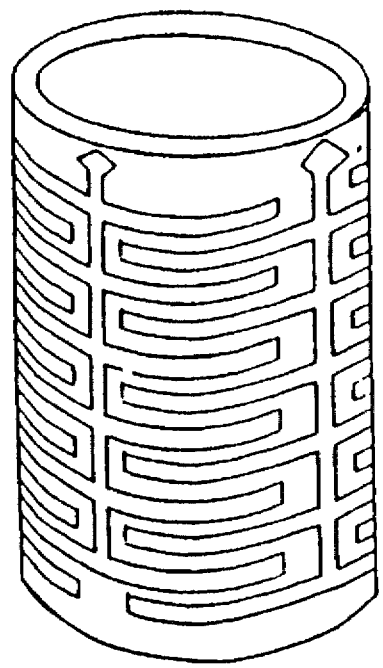
FIG. 45 shows another example of a heater for a cylindrical substrate.
Figure 45:
Figure 45:
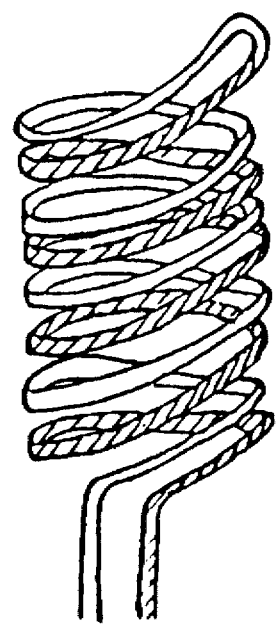

FIG. 44 and FIG. 45 show examples of heaters for use with a cylindrical substrate, where the heater is designed to be inserted into the interior of the cylindrical substrate. When the substrate is cylindrical, uniform heating can be obtained by using a heater which has the form of a coil. Also, by using the heater coiling design shown in FIG. 45, the electromagnetic field arising from the cylindrical current flow can be reduced.

Figure 46:
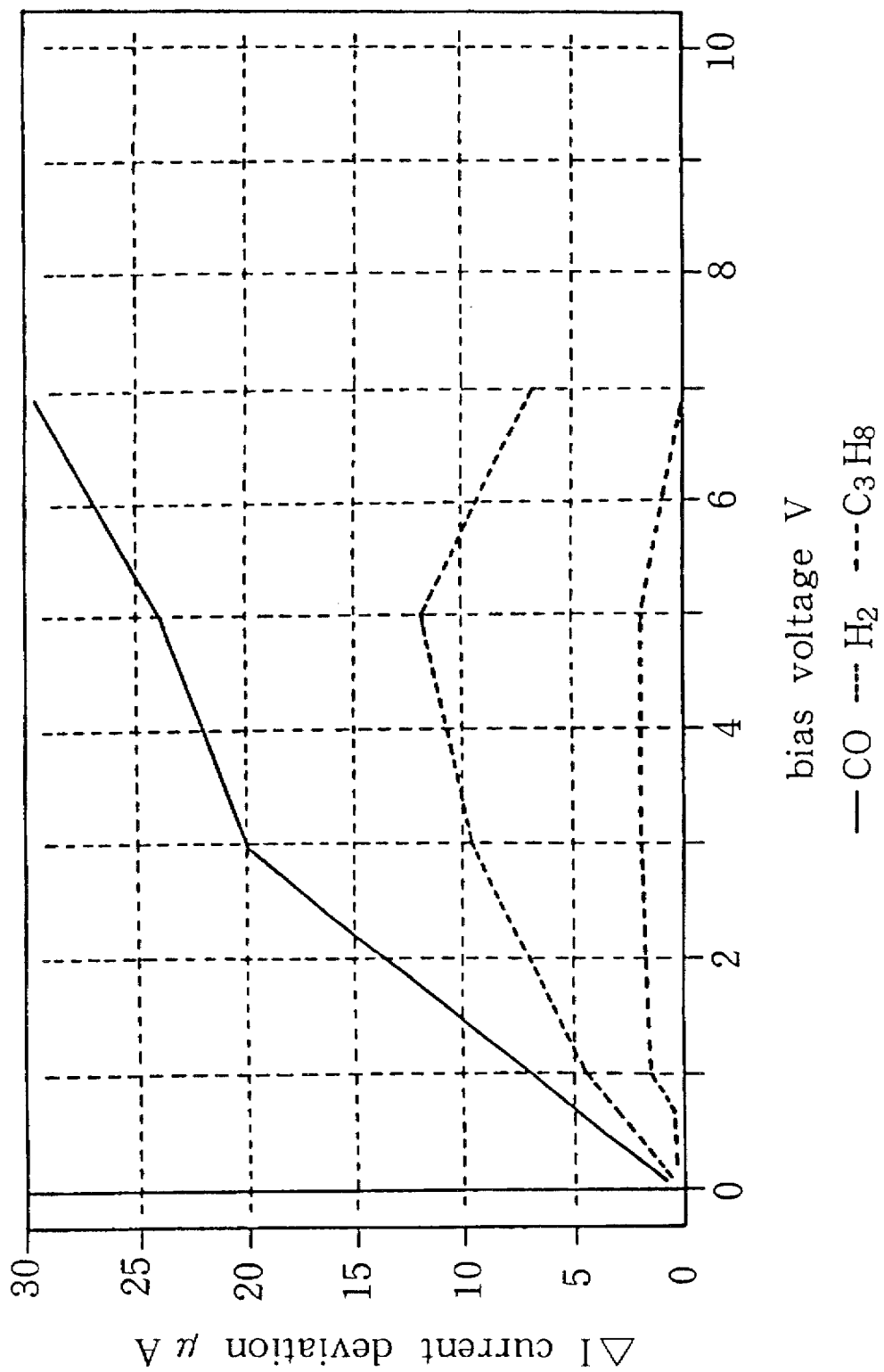
FIG. 46 gives typical characteristics of a gas sensor comprising pressure-bonded CuO and ZnO thick films.

FIG. 46 shows typical characteristics of a gas sensor with the construction shown in FIG. 1 but which is different from the aforementioned examples in that the CuO thick film and the ZnO thick film have been pressure-bonded. This figure shows the amount of change in current as a function of bias voltage when CO, $H_2$ or $C_3H_8$ were respectively introduced.

Figure 47:
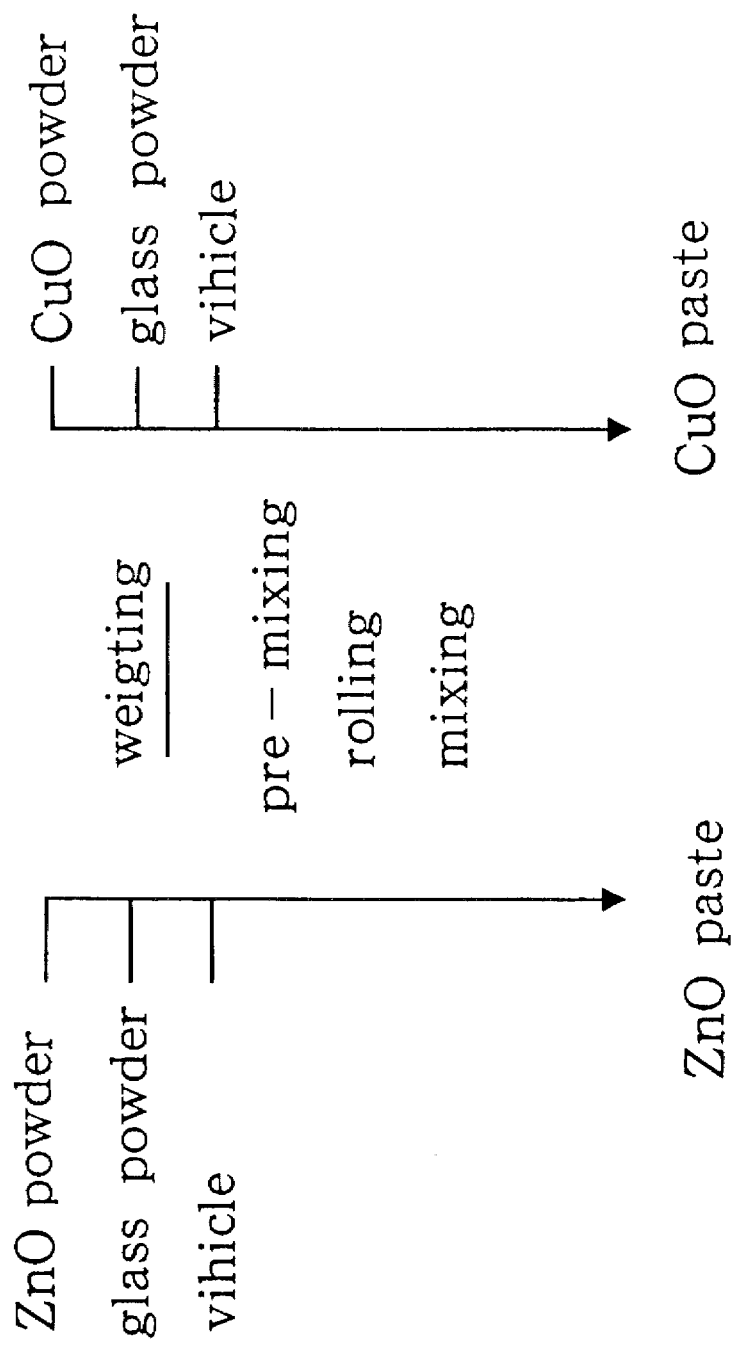
FIG. 47 explains the manufacture of a gas sensor, showing how the pasty substances are prepared.
Figure 48:
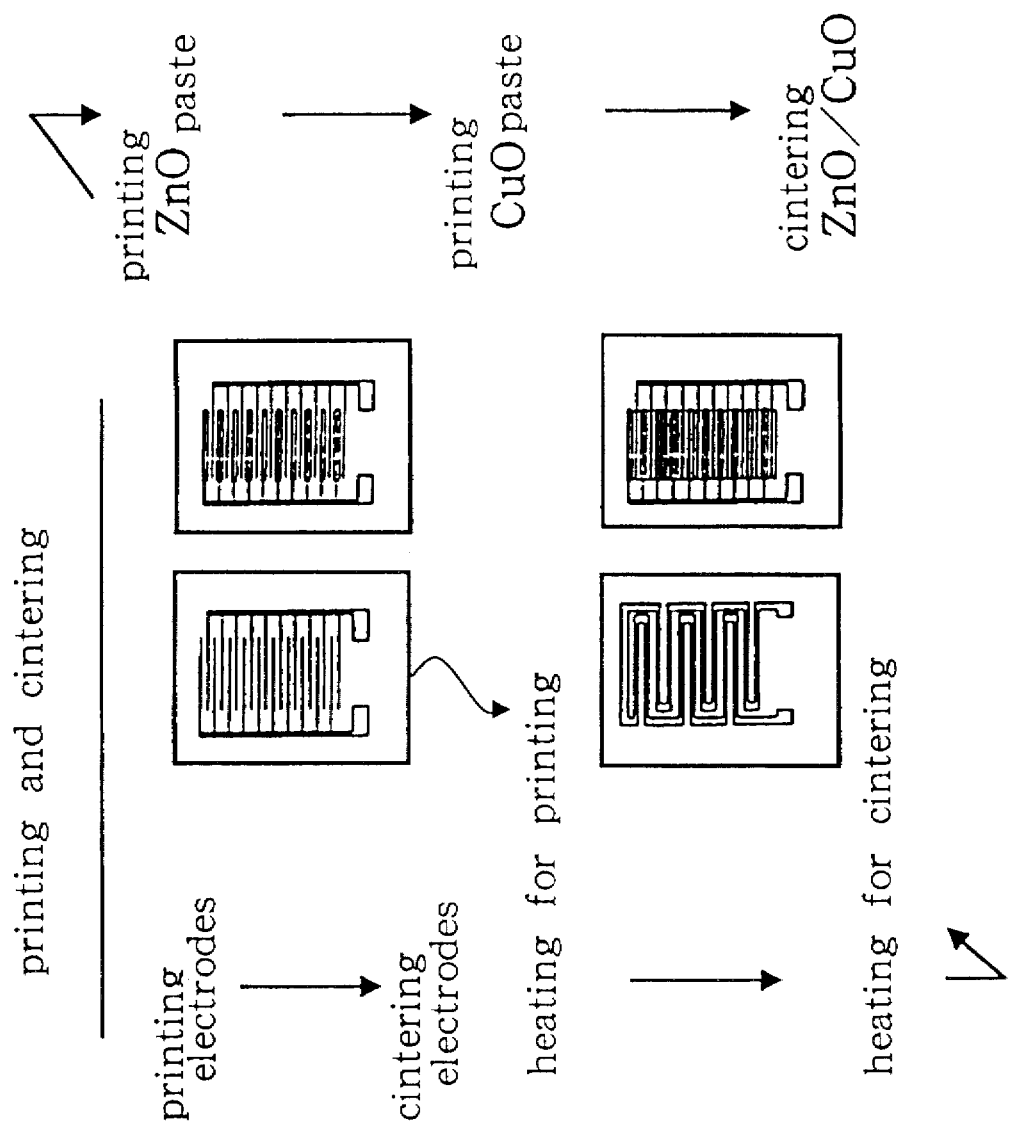
FIG. 48 explains the manufacture of a gas sensor, showing the printing and firing steps involved.

FIG. 47 and FIG. 48 indicate how the gas sensors used for the measurement of these characteristics are manufactured. FIG. 47 shows how the pasty substances are prepared, and FIG. 48 outlines the steps involved in the printing and firing processes.

Figure 49:
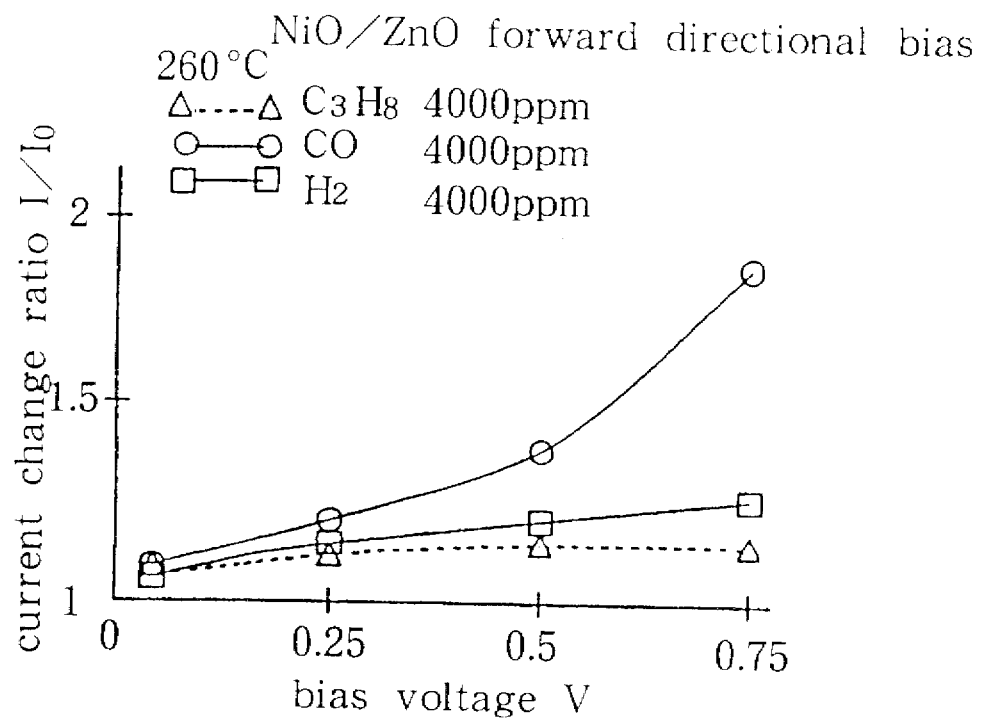
FIG. 49 shows current change ratio as a function of bias voltage when a forward bias has been applied to pressure-bonded NiO and ZnO thick films.
Figure 50:
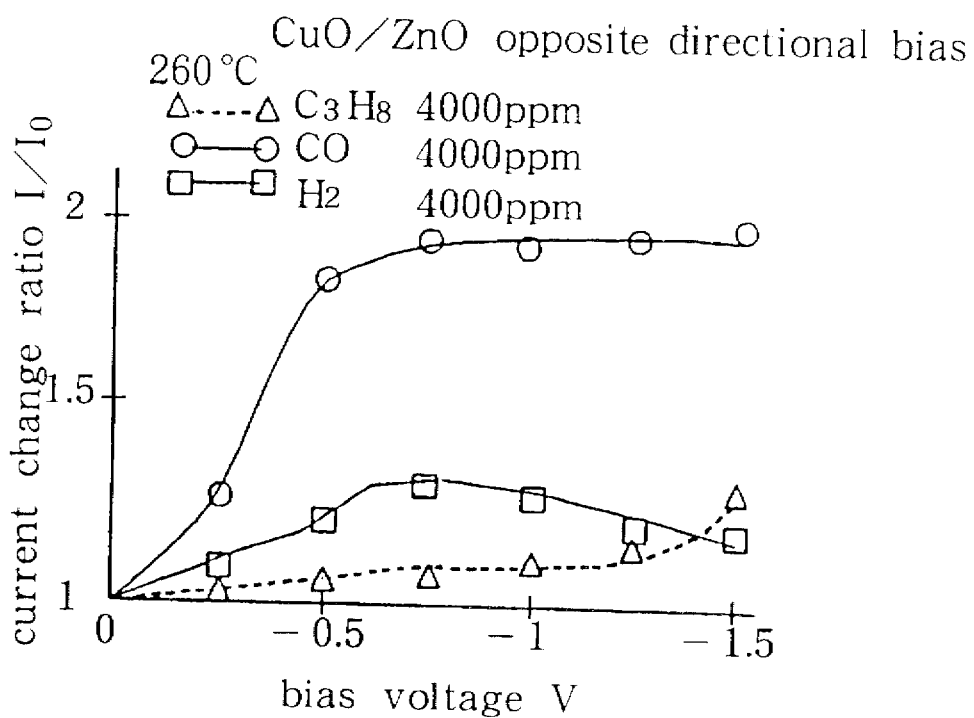
FIG. 50 shows current change ratio as a function of bias voltage when a reverse bias has been applied to pressure-bonded CuO and ZnO thick films.
Figure 51:
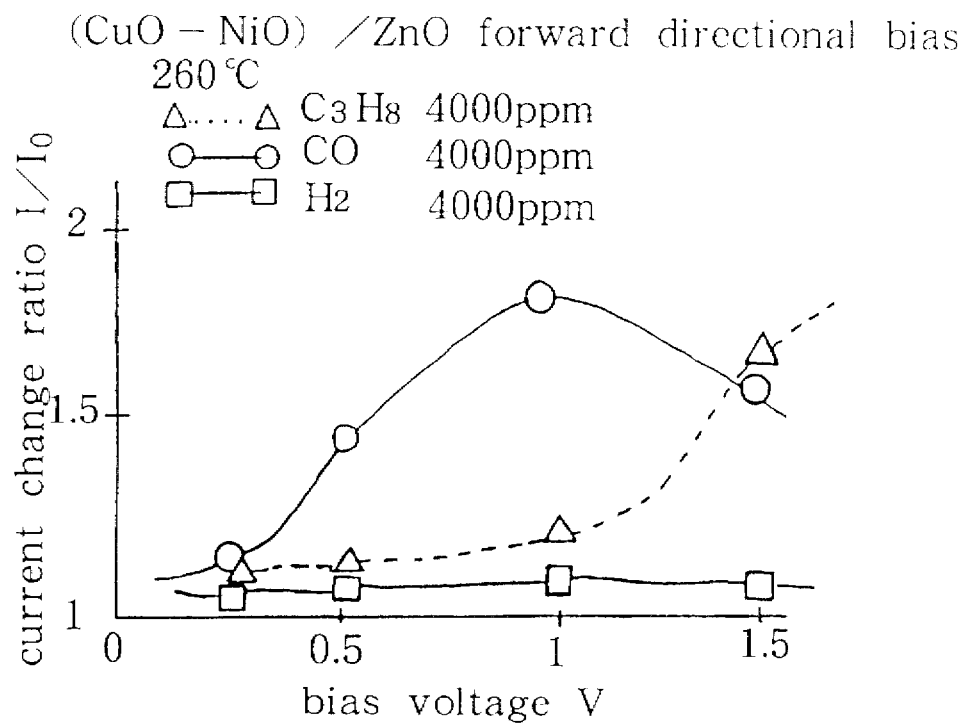
FIG. 51 shows current change ratio as a function of bias voltage when a forward bias has been applied to pressure-bonded CuO-NiO and ZnO thick films.
Figure 52:
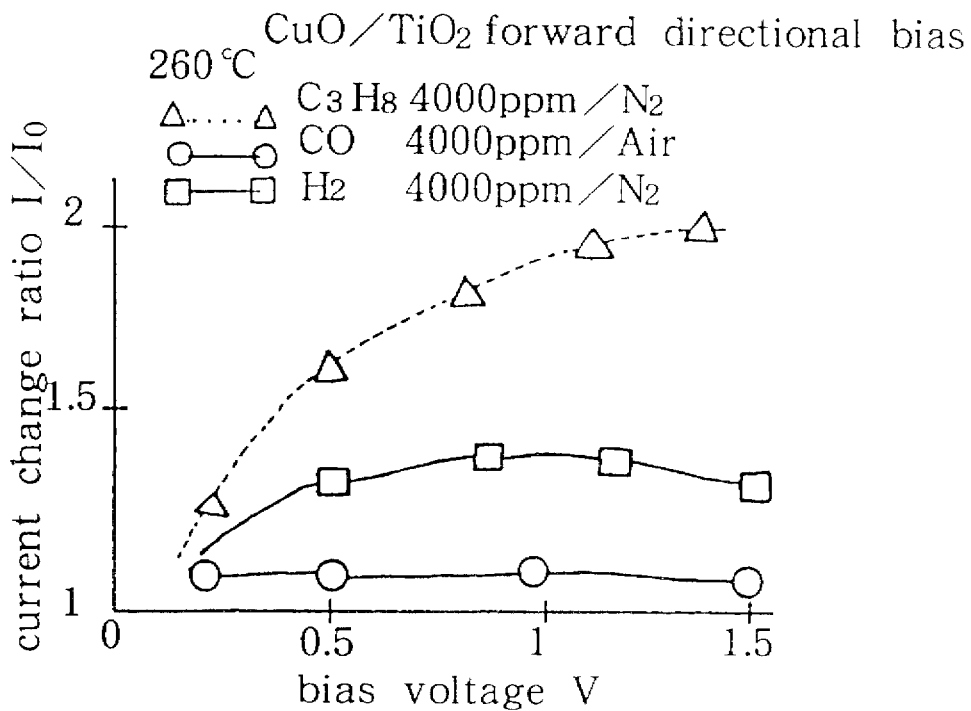
FIG. 52 shows current change ratio as a function of bias voltage when a forward bias has been applied to pressure-bonded CuO and TiO₂ thick films.

FIG. 49 to FIG. 50 show typical characteristics of experimental gas sensors in the detection of CO, $H_2$ and $C_3H_8$. In each case, the current change ratio is shown as a function of bias voltage. FIG. 49 shows this relation when a forward bias was applied to pressure-bonded NiO and ZnO thick films. FIG. 50 shows the same relation when a reverse bias was applied to pressure-bonded CuO and ZnO thick films. FIG. 51 shows this relation when a forward bias was applied to pressure-bonded CuO-NiO and ZnO thick films. Finally, FIG. 52 shows the relation for forward-biased pressure-bonded CuO and $TiO_2$ thick films. The concentrations of CO, $H_2$ and $C_3H_8$ were each 4000 ppm, and the ambient temperature was 260° C.

Sensitivity and selectivity for CO gas were as shown in Table 4. Additives used are shown in Table 4 in brackets.

TABLE 4

| | CO Gas Sensitivity and Selectivity | | |
|---|---|---|---|
| pn | CuO | NiO (LiO$_2$) | CoO (LiO$_2$) |
| ZnO | ⊚ | ○ | ○ |
| TiO$_2$ (Nb$_2$O$_5$) | ○ | △ | △ |
| SnO$_2$ | ○ | ○ | ○ |
| WO$_3$ | ○ | ○ | ○ |

Figure 53:
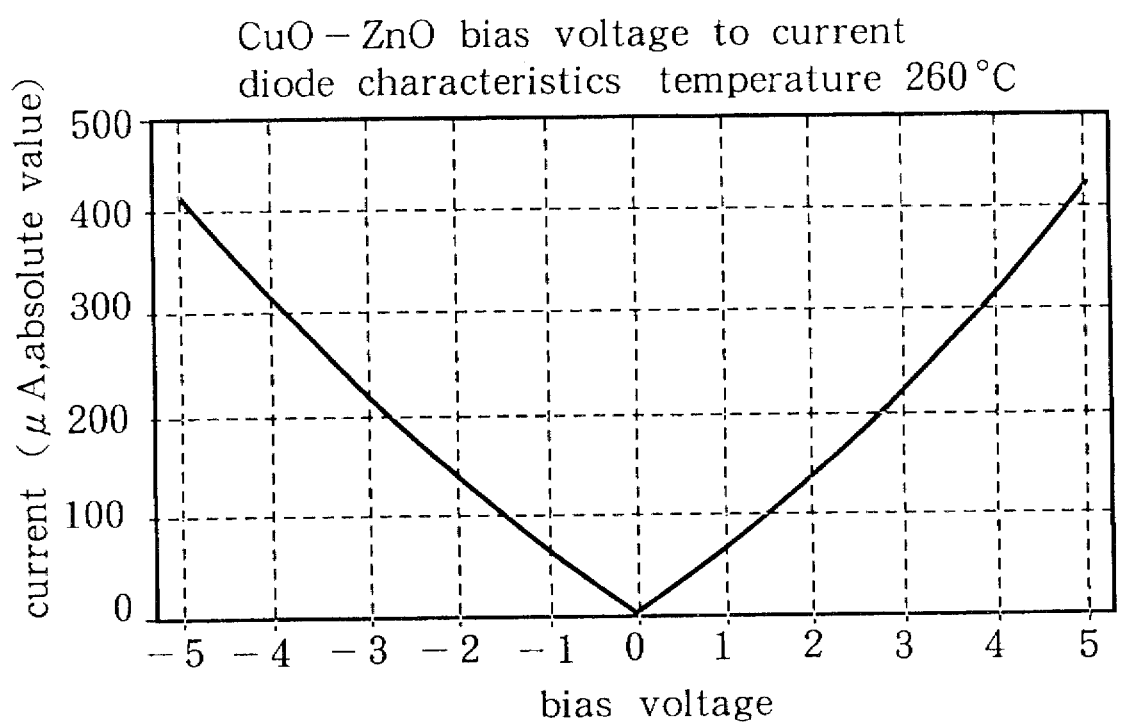
FIG. 53 gives typical current versus bias voltage characteristics of a mixed pn semiconductor thick film.

⊚: sensitivity and selectivity both outstandingly good
○: sensitivity and selectivity both excellent
△: both sensitivity and selectivity exhibited
X: neither sensitivity nor selectivity exhibited FIG. 53 shows typical current versus bias voltage characteristics of a mixed pn semiconductor thick film, where the vertical axis is the absolute value of the current. For this example, a mixture of CuO and ZnO was measured at an ambient temperature of 260° C. As will be seen from FIG. 53, there is rectifying behaviour between the electrodes.

Figure 54:
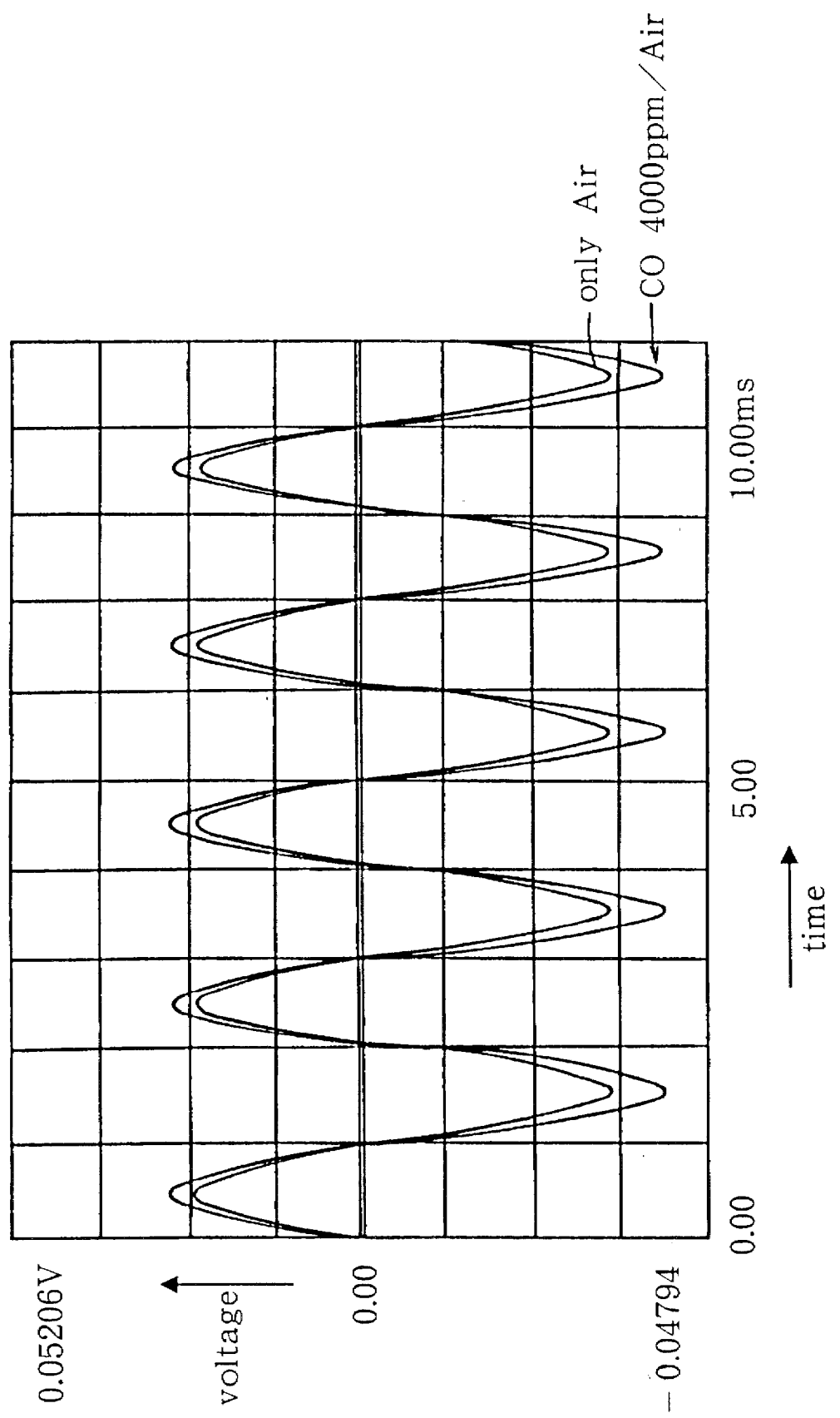
FIG. 54 shows voltage changes when an AC voltage has been applied to a mixed pn semiconductor thick film.

FIG. 54 shows the change in voltage when an AC voltage was applied to the same mixed pn semiconductor thick film as in FIG. 53. As will be seen from FIG. 54, the voltage differs according to whether the atmosphere is air alone or whether 4000 ppm of CO have been mixed with the air.

Figure 55A:
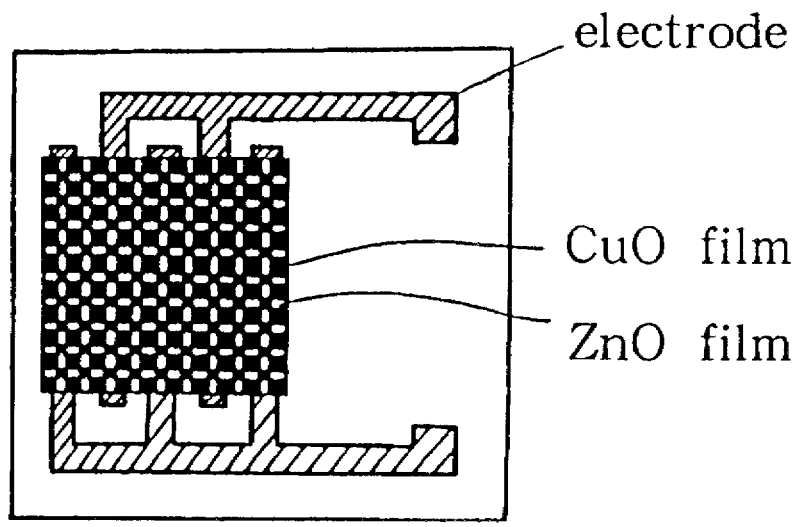
FIG. 55a is a plan view of an example of the structure of a gas sensor where separate p and n materials have been provided.
Figure 55B:
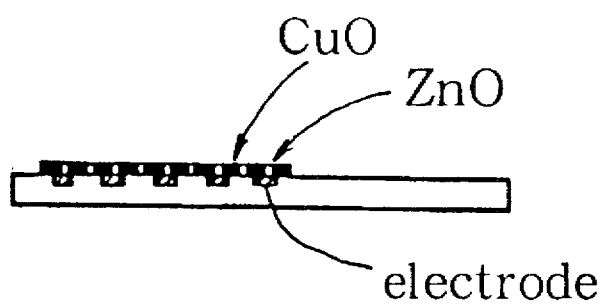
FIG. 55b is the corresponding transverse sectional view.
Figure 56:
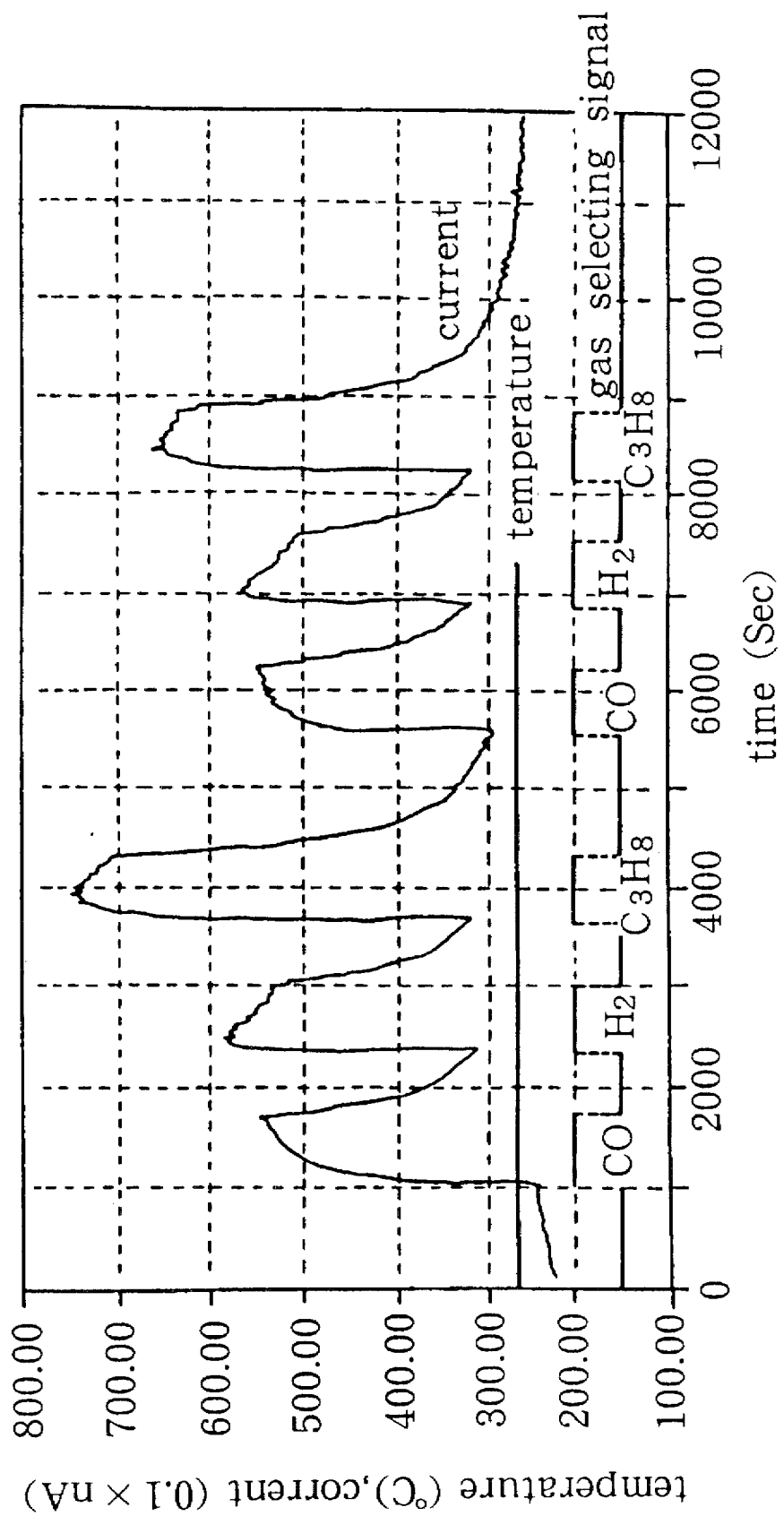
FIG. 56 shows typical characteristics obtained with the structure shown in FIG. 55a and FIG. 55b.

FIG. 55a and FIG. 55b show an example of the structure of a gas sensor wherein p-type regions and n-type regions have been intermixed. Such a structure is analogous to a mixed pn semiconductor film. FIG. 55a is a plan view and FIG. 55b is a transverse sectional view. Typical characteristics obtained with this structure are shown in FIG. 56. The horizontal axis in FIG. 56 is time and the vertical axis gives current and the temperature of the contact regions. These results were obtained using a gas sensor in which CuO and ZnO were arranged so as to be in mutual contact with the surface of comb-type electrodes. A bias voltage of 10 V was applied and measurements made of change in current when CO, $H_2$ and $C_3H_8$ were successively introduced at an ambient temperature of 260° C. In each case, gas concentration was 4000 ppm.

Figure 57:
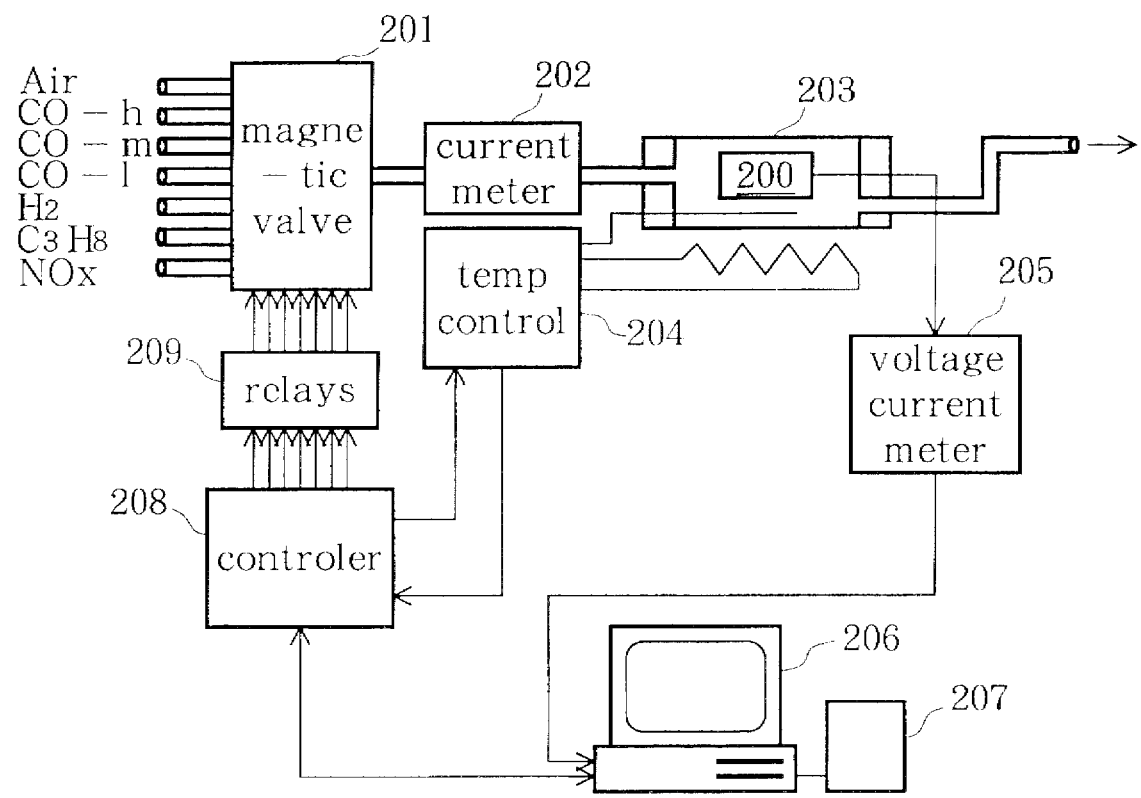
FIG. 57 schematizes the constitution of the test equipment used to investigate the characteristics of experimental gas sensors.

FIG. 57 outlines the test equipment used to investigate the characteristics of the experimental gas sensors.

Measurements were carried out as follows. Gas sensor 200 to be investigated was placed inside tubular furnace 203, and air, CO, $H_2$ or $C_3H_8$ fed to this tubular furnace 203 by way of solenoid valve 201 and mass flow meter 202, and their temperature controlled by temperature controller 204. Voltages applied to gas sensor 200 being investigated and the resulting currents were measured by voltammeter 205, and these measured values were stored in external device 207 after processing by personal computer 206.

Solenoid valve 201 is constituted so that it can select air, $H_2$, $C_3H_8$, NO$_x$, or any of three levels of CO, and supply any of these to tubular furnace $_2O_3$, and is operated by means of control signals sent from controller 208 via relay 209. Personal computer 206 takes in the values of current detected by voltammeter 205, and after a suitable lapse of time, outputs a control signal for gas changeover to controller 208.

Possible Industrial Uses

As has now been explained, gas sensors according to this invention have outstanding characteristics and are suited to mass production. Moreover, this invention is able to provide gas sensors which exhibit stable characteristics, and with which good sensor performance is obtained by having (i) improved circulation of the sample gas around the contact region and (ii) increased area of contact between the semiconductor contact region and the gas. This invention can be utilized for the detection of carbon monoxide, hydrogen, hydrocarbons and other target gases, and can be effectively used in general domestic or business premises, workings where mining or other underground operations are carried out, industrial sites where gases are manufactured or refined, and facilities where petroleum products are transported or refined, etc. In addition, it will be extremely effective when utilized in process control based on gas detection.

We claim:

1. A gas sensor comprising:
   a solid having p-type and n-type semiconductor particles in mutual contact, forming contact regions,
   two electrodes connected to the solid, and
   means for introducing to the contact regions a gas containing the gas to be detected.

2. A gas as set forth in claim 1 wherein the material of the p-type semiconductor particles is one or more materials selected from the group consisting of CuO, NiO, CoO, $Cr_2O_3$, $Cu_2O$, $MoO_2$, $Ag_2O$, $Bi_2O_3$, $Pr_2O_3$, MnO and SiC.

3. A gas sensor as set forth in claim 1 wherein the material of the n-type semiconductor particles is one or more materials selected from the group consisting of MgO, $Al_2O$, $SiO_2$, $V_2O_5$, $Fe_2O_3$, SrO, $Nb_2O_5$, $Nb_2O_4$, $Nb_2O_3$, BaO, $Ta_2O_3$, $Ta_2O_5$, CeO, ZnO, $TiO_2$, $SnO_2$, $WO_3$, $Nd_2O_3$, SiC, $BaTiO_3$, $PbTiO_3$, and $SrTiO_3$.

4. A gas sensor as set forth in claim 1, further comprising means for heating to a temperature at which the p-type semiconductor and the n-type semiconductor will operate as semiconductors.

5. A gas sensor as in claim 1 further comprising:
   a power supply connected to the two electrodes and means for detecting changes in a current flowing through these electrodes.

6. A gas sensor as set forth in claim 5 wherein the power supply is an AC power supply.

7. A gas sensor as set forth in claim 1, further comprising an insulating material substrate, wherein the solid is a thick film formed on the insulating material substrate, and wherein at least one of the two electrodes is a conductor film formed on a surface of the substrate.

8. A gas sensor as set forth in claim 7 wherein the substrate is a ceramic substrate and the thick film is porous.

9. A gas sensor as set forth in claim 7 wherein the substrate is porous.

10. A gas sensor as set forth in claim 7 wherein the substrate is porous and the thick film is porous.

11. A gas sensor as in claim 7 further comprising:

a power supply connector to the two electrodes and means for detecting changes in a current flowing through these electrodes.

12. A gas sensor as set forth in claim 11 wherein the power supply is an AC power supply.

13. A gas sensor manufacturing method comprising the steps of kneading particles of p-type semiconductor material and particles of n-type semiconductor material to form a pasty substance, forming electrodes on a surface of an electrically insulating substrate, coating the pasty substance in contact with the electrodes, and firing the pasty substance in the form of a thick film.

14. A gas sensor manufacturing method comprising the steps of:

forming electrodes on a surface of an electrically insulating substrate;

spray coating a homogeneously mixed substance containing particles of p-type semiconductor material and also particles of n-type semiconductor material to form a thick film in contact with the electrodes.

15. A gas sensor manufacturing method comprising the steps of kneading particles of p-type semiconductor material and particles of n-type semiconductor material to form a pasty substance;

forming electrodes on a surface of an electrically insulating substrate;

printing the pasty substance in contact with the electrodes; and firing the pasty substance in the form of a thick film.

* * * * *